(12) United States Patent
Tang et al.

(10) Patent No.: US 7,939,613 B2
(45) Date of Patent: May 10, 2011

(54) FLUORESCENT WATER-SOLUBLE CONJUGATED POLYENE COMPOUNDS THAT EXHIBIT AGGREGATION INDUCED EMISSION AND METHODS OF MAKING AND USING SAME

(75) Inventors: Benzhong Tang, Hong Kong (CN);
Yuning Hong, Hong Kong (CN);
Matthias Haeussler, Bad Lauchstaedt (DE); Hui Tong, Uppsala (SE);
Yongqiang Dong, Beijing (CN); Zhen Li, Wuhan (CN); Changmin Xing, Beijing (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 472 days.

(21) Appl. No.: 12/000,130

(22) Filed: Dec. 10, 2007

(65) Prior Publication Data

US 2008/0220407 A1  Sep. 11, 2008

Related U.S. Application Data

(63) Continuation-in-part of application No. 11/408,846, filed on Apr. 21, 2006.

(60) Provisional application No. 60/673,562, filed on Apr. 22, 2005, provisional application No. 60/929,364, filed on Jun. 25, 2007, provisional application No. 60/873,431, filed on Dec. 8, 2006.

(51) Int. Cl.
| | |
|---|---|
| C08F 220/12 | (2006.01) |
| G01N 15/06 | (2006.01) |
| G01N 33/53 | (2006.01) |
| C12Q 1/70 | (2006.01) |
| C12Q 1/68 | (2006.01) |

(52) U.S. Cl. ............... 526/329.1; 435/5; 435/6; 435/7.1; 435/7.2; 422/68.1

(58) Field of Classification Search ............... 526/329.1; 435/5, 6, 7.1, 7.2; 422/68.1
See application file for complete search history.

(56) References Cited

U.S. PATENT DOCUMENTS

| | | | |
|---|---|---|---|
| 4,203,967 | A | 5/1980 | Gallo-Torres |
| 4,729,947 | A | 3/1988 | Middendorf et al. |
| 5,131,916 | A | 7/1992 | Eichenauer et al. |
| 5,346,603 | A | 9/1994 | Middendorf et al. |
| 5,410,030 | A | 4/1995 | Yue et al. |
| 5,436,134 | A | 7/1995 | Haugland et al. |
| 5,627,027 | A | 5/1997 | Waggoner |
| 5,716,855 | A | 2/1998 | Lerner et al. |
| 6,143,151 | A | 11/2000 | Middendorf et al. |
| 6,143,153 | A | 11/2000 | Middendorf et al. |
| 6,316,267 | B1 | 11/2001 | Bhalgat et al. |
| 6,465,208 | B1 | 10/2002 | Rogers et al. |

(Continued)

OTHER PUBLICATIONS

Iyoda, Masahiko et al. Chemistry Letters (1988), (1), 149-52.*

(Continued)

*Primary Examiner* — Jezia Riley
(74) *Attorney, Agent, or Firm* — The Nath Law Group

(57) ABSTRACT

The presently described subject matter is directed to water-soluble conjugated polyene compounds that exhibit aggregation induced emission, as well as to water dispersible, fluorescent, polymeric microparticles and/or nanoparticles comprising the water-soluble conjugated polyene compounds. Also provided are methods of making and using the compounds and particles. The described conjugated polyene compounds are useful as bioprobes for the detection biomacromolecules, as well as in the manufacture of sensors.

25 Claims, 22 Drawing Sheets

U.S. PATENT DOCUMENTS

| | | |
|---|---|---|
| 6,607,918 B2 | 8/2003 | LaGraff et al. |
| 6,818,642 B2 | 11/2004 | Grundler |
| 6,822,096 B2 | 11/2004 | Kato |
| 6,897,297 B1 | 5/2005 | Pepinsky |
| 6,914,250 B2 | 7/2005 | Seville |
| 6,969,615 B2 | 11/2005 | Knezevic et al. |
| 7,015,002 B2 | 3/2006 | Isobe |
| 7,109,314 B2 | 9/2006 | Shinoki et al. |
| 2006/0165621 A1 | 7/2006 | Dubertret et al. |
| 2006/0240565 A1 | 10/2006 | Tang et al. |

OTHER PUBLICATIONS

Tong et al. Fluorescent "light-up" bioprobes based on tetraphenylethylene derivatives with aggregation-induced emission characteristics. Chem. Commun. (2006) 3705-3707.

Palayangoda et al. Carbazole-Based Donor-Acceptor Compounds: Highly Fluorescent Organic Nanoparticles. Organic Letters. 2008. vol. 10, No. 2. 281-284.

Furstenberg et al. Structure—Fluorescence Contrast Relationship in Cyanine DNA Intercalators: Toward Rational Dye Design. Chem. Eur. J. 2007, 13, 8600-8609.

Suzuki et al. Design and Synthesis of Intramolecular Charge Transfer-Based Fluorescent Reagents for the Highly-Sensitive Detection of Proteins. J. AM. Chem. Soc. 2005, 127, 17799-17802.

Ning et al. Aggregation-Induced Emission (AIE)-active Starburst Triarylamine Fluorophores as Potential Non-dopes Red Emitters for Organic Light Emitting Diodes and Cl2 Gas Chemodosimeter. Adv. Funct. Mater. 2007, 17, 3799-3807.

Xie et al. A Class of Nonplanar Conjugated Compounds with Aggregation-Induced Emission: Structural and Optical Properties of 2,5-Diphenyl-1,4-distyrylbenzene Derivatives with All Cis Double Bonds. J. Phys. Chem. B 2006, 110, 20993-21000.

Tong et al. Color-Tunable, Aggregation-Induced Emission of a Butterfly-Shaped Molecule Comprising a Pyran Skeleton and Two Cholesteryl Wings. J. Phys. Chem. B 2007, 111, 2000-2007.

Iyer et al. The Transcriptional Program in the Response of Human Fibroblasts to Serum. Science 283, 83 (1999), 83-87.

Hu et al. Preparation of Fluorescent Particles with Long Excitation and Emission Wavelengths Dispersible in Organic Slovents. Langmuir 2004, 20, 7463-7443.

Dinsmore et al. Three-dimensional confocal microscopy of colloids. Applied Optics. vol. 40, No. 24. Aug. 20, 2001. 4152-4159.

Lakowicz et al. Release of the self-quenching of fluorescence near silver metallic surfaces. Analytical Biochemistry 320 (2003) 13-20.

Gao et al. Preparation of a novel polymeric fluorescent nanoparticle. Colloid Polym Sci (2002) 280: 653-660.

\* cited by examiner

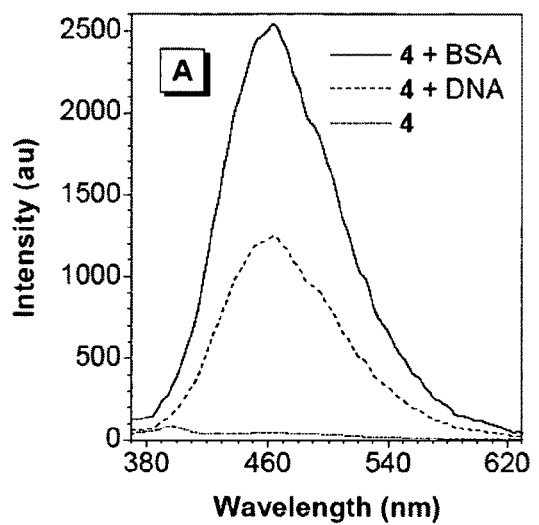
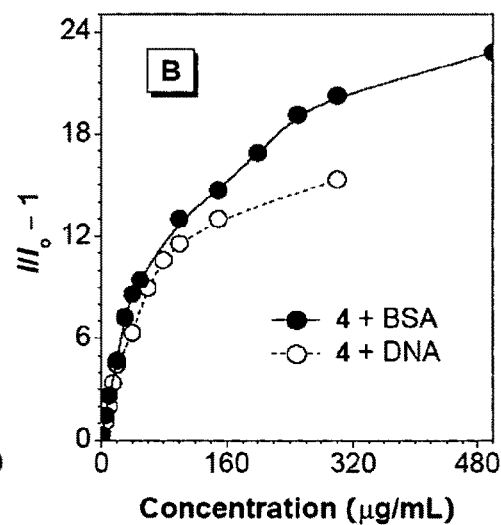
FIG. 6A             FIG. 6B

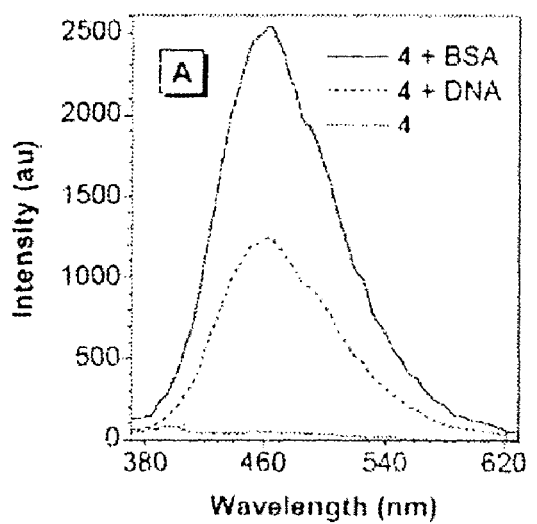 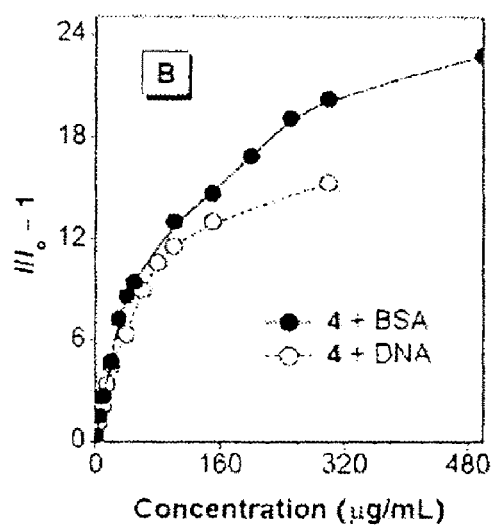
FIG. 12A         FIG. 12B

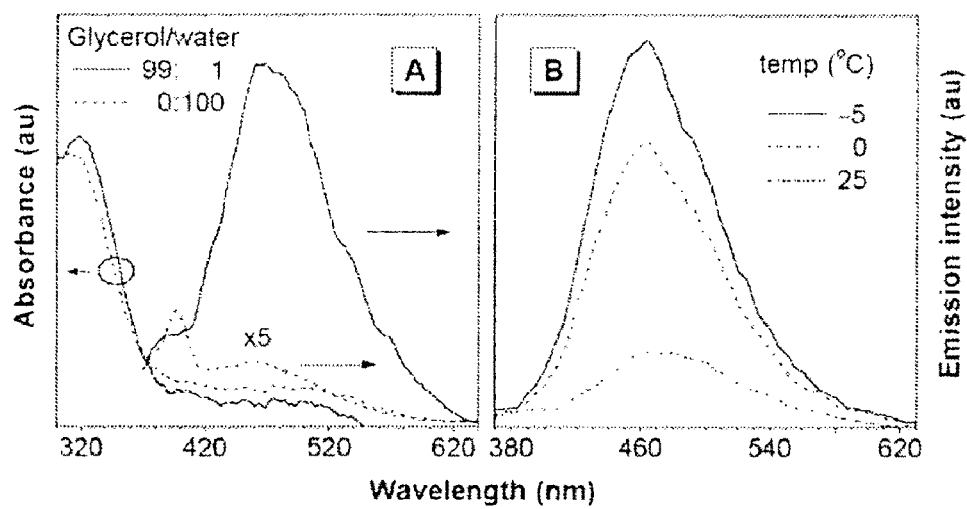
FIG. 13A  FIG. 13B

Fig 16A & B (inset)

FLUORESCENT WATER-SOLUBLE CONJUGATED POLYENE COMPOUNDS THAT EXHIBIT AGGREGATION INDUCED EMISSION AND METHODS OF MAKING AND USING SAME

CROSS REFERENCE TO RELATED APPLICATION

Pursuant to 35 U.S.C. §119(e), this application claims the benefit of Provisional Application No. 60/873,431 filed on Dec. 8, 2006 and to Provisional Application No. 60/929,364 filed on Jun. 25, 2007, and is a Continuation-in-Part Application of U.S. Published Patent Application No. 2006/0240565, published on Oct. 26, 2006, which was filed on Apr. 21, 2006 and claims priority to U.S. Provisional Application No. 60/673,562 filed on Apr. 22, 2005. All of the foregoing applications are hereby incorporated by reference herein in their entirety.

FIELD OF THE INVENTION

The presently described subject matter relates generally to compounds that exhibit aggregation induced emission, and more particularly to water-soluble conjugated polyene compounds that exhibit aggregation induced emission.

BACKGROUND OF THE INVENTION

Fluorescence (FL) techniques have emerged as a mainstream research and development area in science and engineering, particularly in the field of biochemical and biological science. Currently, fluorescent molecules are used as probes for DNA sequencing, fluorescence-activated cell sorting, high-throughput screening, and clinical diagnostics.

Fluorescence-based techniques offer high sensitivity, low background noises and broad dynamic ranges. A great number of fluorescent probes have been investigated and are already widely used in biotechnology. Many of them show favorable spectral properties of visible absorption and emission wavelength, high extinction coefficients, and reasonable quantum yields. Upon complexation with proteins and DNA, the fluorescence of the bioprobes can be enhanced/quenched and/or red/blue-shifted, thus enabling visual observation of the biomacromolecular species. Among these, the most useful probes are those that act as "turn-on" sensors, whose fluorescence is activated by the analytes.

Several probes for DNA detection based on fluorescent enhancement have been developed such as phenanthridine and acridine derivatives. Middendorf et al. have reported on ethidium bromide (EB), a well-known phenanthridine derivative, which has already been widely used for DNA-sequencing (U.S. Pat. No. 4,729,947, U.S. Pat. No. 5,346,603, U.S. Pat. No. 6,143,151, U.S. Pat. No. 6,143,153). FL enhancement induced by proteins can be attributed to the interaction with hydrophobic regions of proteins, such as NanoOrange (Molecular Probes, Inc., U.S. Pat. No. 6,818,642) and Nile red (U.S. Pat. No. 6,897,297, U.S. Pat. No. 6,465,208), or reaction with amine groups of proteins in the presence of cyanide or thiols, such as fluorescamine (U.S. Pat. No. 4,203,967) and o-phthaldialdehyde (U.S. Pat. No. 6,969,615, U.S. Pat. No. 6,607,918). The FL of cyanine dyes has been found to increase dramatically upon complexation with DNA and proteins. (U.S. Pat. No. 5,627,027, U.S. Pat. No. 5,410,030). Haugland et al. have reported unsymmetrical cyanine dyes, which possess superior fluorescent characteristics when complexed with nucleic acids (U.S. Pat. No. 5,436,134). The SYPRO® dyes are merocyanine dyes that are essentially non-fluorescent when free in solution but become intensely fluorescent in hydrophobic environments (e.g. SYPRO®Red and SYPRO®Orange dyes of Molecular Probes, Inc., U.S. Pat. No. 6,914,250, U.S. Pat. No. 6,316,267). Water-soluble cyanine dyes, such as Cy3 and Cy5, are commonly used in labeling of DNA or RNA for micoarray (V. R. Iyer et al., Science, 1999, 283, 83). Cy3 and Cy5 have merits of high fluorescence intensity and emission even in solid state, whereas, they are quite unstable and show insufficient detection sensitivity (U.S. Pat. No. 7,015,002).

As described in U.S. Pat. No. 7,109,314, a good fluorescent dye should possess a high fluorescent quantum yield and molecular absorption coefficient, as well as good solubility in aqueous media and stability under ambient conditions. However, most of the dyes discussed above are lipophilic, which are at best, only dispersible in aqueous media. For example, Nile Red, a dye used to stain proteins, should be first dissolved in acetone and then mixed rapidly with water immediately prior to use (J. R. Daban et al, Anal. Biochem, 1991, 199, 169).

Additionally, substantially all of the above-described fluorescent dyes suffer from the problem of aggregation-caused quenching (ACQ). Due to their lipophilic character, these fluorescent dyes are prone to aggregate when dispersed in aqueous media or when bound to biological macromolecules. The close proximity of the chromophores often induces a non-radiative energy transfer mechanism that results in self-quenching of the luminescence. This self-quenching drastically reduces the dyes' fluorescent signal thereby prohibiting their use as efficient bioprobes or biosensors.

Substantial effort has been made to mitigate aggregate formation of these dyes (J. R. Lakowicz, et al. Anal Biochem, 2003, 320, 13). However, only a small number of researchers have focused on the design and synthesis of novel organic molecules or polymers that do not suffer from fluorescent quenching, and moreover, even display enhanced light emission upon aggregation.

Recently, aggregation-induced emission (AIE) has been observed. This phenomena is exactly opposite of ACQ. Some non-emissive dyes can be induced to emit efficiently by the aggregate formation. AIE molecules with high quantum yields $\Phi_F$ (up to 0.85) and various emission colors (blue, green, yellow and red) have been reported. While the AIE dyes have been used for the construction of efficient optical and photonic devices, the possibility of employing them as bioprobes for detecting biopolymers have been virtually unexplored. Accordingly, there remains a great need for water-soluble "light-up" compounds and probes, for example, for the detection of biomacromolecules such as DNA and proteins.

There is a growing demand for new sensors useful for detecting/sensing biomacromolecules. Sensors based on detecting fluorescence of an analyte such as a biomacromolecule are highly sensitive, thereby lowering detection limits.

Many known fluorescent materials accomplish the detection of saccharides by the competing intramolecular interaction of an amine functionality with a boronic acid pendant. Less effort has been spent on the detection of other biological compounds. Furthermore, vapor-sensing compounds and devices are often manufactured from the expensive platinum salts and complexes and/or in combination with palladium. They are based mainly on a color shift from dark-red to light-red, making it difficult to visually sense the color shift. Sensors exhibiting an on-off change in their luminescent color rather then a color shift will be thus not only advantageous but also more sensitive. To applicants' knowledge, the only known "on-off" example was shown by Kato (U.S. Pat. No. 6,822,096), who utilized the luminescence change from the invisible near-infrared to the visible red of binuclear platinum (II) complexes. However, these complexes only shift the emitted wavelength out of the visible spectrum.

Fluorescent materials, including inorganic semiconductor quantum dots, organic and metallorganic dyes, dye-doped silica or polymer particles, have currently attracted great attention in a wide variety of high-technology applications such as high-throughput screening, ultra-sensitive assays, optoelectronics, and living cell imaging. Colloidal quantum dots (hundreds to thousands of atoms) are traditionally made from crystals of IIA-VIA or IIIB-VB elements (PbS, CdSe, etc.) or other semiconductors. The heavy metals therein are intrinsically toxic to the researchers and the experimental systems (e.g., living cells), as well as generating a toxic waste stream into the environment. Organic and metallorganic dyes generally consist of π-conjugated ring structures such as xanthenes, pyrenes or cyanines, with emissions across the spectrum from UV to the near infrared (~300-900 nm) and may be fine tuned to particular wavelengths or applications by changing the chemistry of their substituent groups. The size of individual dye molecules is very small (~1 nm), which causes non-specific labeling and high background signals as dyes diffuse away from their intended targets. Spectrally, organic dyes tend to have fairly wide absorption and emission spectra (FWHM ~50 nm), which can lead to spectral overlap and re-absorption when using multiple dye species simultaneously. In normal use, dye molecules are exposed to a variety of harsh environments and often suffer from photobleaching and quenching due to the interactions with solvent molecules and reactive species such as oxygen or ions dissolved in solution.

In order to create more robust emitters with enhanced brightness and stability, researchers have developed composite nano- and micro-particles consisting of dye molecules and silica or polymer matrix. Thus the encapsulated dye molecules can be protected from external perturbations, with reducing stochastic blinking, photobleaching, and quenching. Dye-loaded polymer particles are superior to their silica counterpart in terms of the versatile chemical compositions, tunable surface chemistry suited for biocompatibility and bioconjugation, facile preparation, and easy control of the particle size and size distribution.

Gao et al. have incorporated pyrene dyes into polystyrene particles using a normal microemulsion approach, leading to a 40-fold increase in emission intensity with respect to the pure dye at the identical concentration (H. Gao et al., Colloid Polym. Sci. 2002, 280, 653). Dinsmore et al. swelled poly (methyl methacrylate) particles and absorbed a rhodamine dye into them for usage in a confocal microscopic study of colloidal dispersions (A. D. Dinsmore et al., Appl. Opt. 2001, 40, 4152). U.S. Pat. No. 5,716,855 disclosed fluorescent particles containing anthracene- or naphthacene-derivatived dyes aiming to the application as biological markers.

Up to now, most of the organic dyes commercially available, including the above mentioned dyes as well as ethidium bromide (U.S. Pat. No. 4,729,947, U.S. Pat. No. 5,346,603, U.S. Pat. No. 6,143,151, and U.S. Pat. No. 6,143,153), Nile red (U.S. Pat. No. 6,897,297 and U.S. Pat. No. 6,465,208), fluorescamine (U.S. Pat. No. 4,203,967), o-phthaldialdehyde (U.S. Pat. No. 6,969,615 and U.S. Pat. No. 6,607,918), Cyanine dyes (U.S. Pat. No. 5,627,027 and U.S. Pat. No. 5,410,030), etc. are emissive only in their solution state, whereas emission is quenched in aggregation states (e.g., high dye concentration state, film state, solid state, etc.). This is attributed to the mechanism of nonradiative energy transfer between the closely packed chromophores, thus resulting in self-quenching of the fluorescence. Thus, the loading concentration of dyes in the polymer particles cannot be sufficiently high and accordingly the intensity of fluorescence is considerably limited.

With respect to the polymers for dye encapsulation, the currently available species are mainly hydrophobic polystyrene and less hydrophobic poly(methyl methacrylate), as mentioned hereinabove. The hydrophobic nature of these particles commonly leads to clustering and non-specific binding of biological materials, which considerably limits their application in aqueous environment of biology and other fields. Additionally, these particles are prepared and dispersed in organic solvent. For example, Hu et al. prepared poly(methyl methacrylate) fluorescent particles through dispersion polymerization in the mixture of hexane and ethanol (H. Hu et al., Langmuir 2004, 20, 7436). The solvent-dispersible polymer particles are difficult to disperse stably in aqueous media.

The presently described series of linear and cyclic π-conjugated organic compounds (hereinafter polyenes) have been designed and synthesized with different chromophores including tetraphenylethylene, siloles, fulvene, butadienes, and 4H-pyrans. The emission color of these new polyenes ranges from blue to red arising from the different chromophoric structures. Their fluorescent behavior features the aggregation-induced emission (AIE) phenomenon, which turns the dyes from faint-emitters when molecularly dissolved into strong luminophors when aggregated or in the solid state. All these features make the presently described AIE-active molecules excellent candidates for use as bioprobes and in polymeric particles, sensors and detection devices.

SUMMARY OF THE INVENTION

The presently described subject matter is directed to water-soluble conjugated polyenes which exhibit aggregation induced emission and are useful as bioprobes and for manufacturing sensors. The emission color of these water-soluble conjugated polyenes ranges from blue to red arising from the different chromophoric structures. They exhibit aggregation-induced emission (AIE) (i.e., increased fluorescence) upon addition of a non-aqueous solvent. Their luminescent behavior features the aggregation-induced emission (AIE) phenomenon, which turns the dyes (water-soluble conjugated polyenes) from faint-emitters when molecularly dissolved in an aqueous solvent, i.e., water, into strong luminophors when aggregated or in solid state. Stated differently, when the compounds are dissolved in aqueous solvents, they are substantially nonemissive ("off") while when a non-aqueous solvent is added, they aggregate and emit intensely ("on"). The quantum efficiency increases when the amount of non-aqueous solvent is increased. The presently described water-soluble conjugated polyene compounds are useful as "turn-on" fluorescence sensors. In addition, the presently described subject matter is directed to water-dispersible fluorescent polymer particles, i.e., micro-particles and/or nano-particles, comprising the described water-soluble conjugated polyenes, for example, a tetraphenylethylene ("TPE").

Based on this proposed mechanism, several of the presently described AIE-active dyes which exhibit fluorescent "turn-on" property when bound to biomacromolecules were investigated. A group of water-soluble AIE molecules were designed and synthesized. When the presently described water-soluble AIE molecules are dissolved in water or phosphate buffer saline (PBS), the solution is virtually nonemissive. However, the fluorescence increases significantly in the presence of proteins and DNA. There is a linear relationship between fluorescent intensity and the concentration of analytes in a certain range, which is of great importance in protein and DNA assays.

Furthermore, the presently described AIE water-soluble molecules are organic compounds, which make them easily accessible and much more economical compared to platinum or transition metal-containing counterparts. All of the presently described AIE-active water-soluble molecules are advantageous in that they can be synthesized in many structural forms and can be easily substituted with a variety of functional groups.

In addition, the presently described AIE-active water-soluble molecules are very stable. Virtually no change is observed in their photoluminescence spectra when they are stored under ambient temperature without any protection from light and air for more than two months. This is distinctly different from other dye molecules, which suffer from photobleaching when exposed to room illumination.

In an embodiment, the present subject matter relates to a water-soluble conjugated polyene compound comprising a backbone structure of a formula selected from the group consisting of:

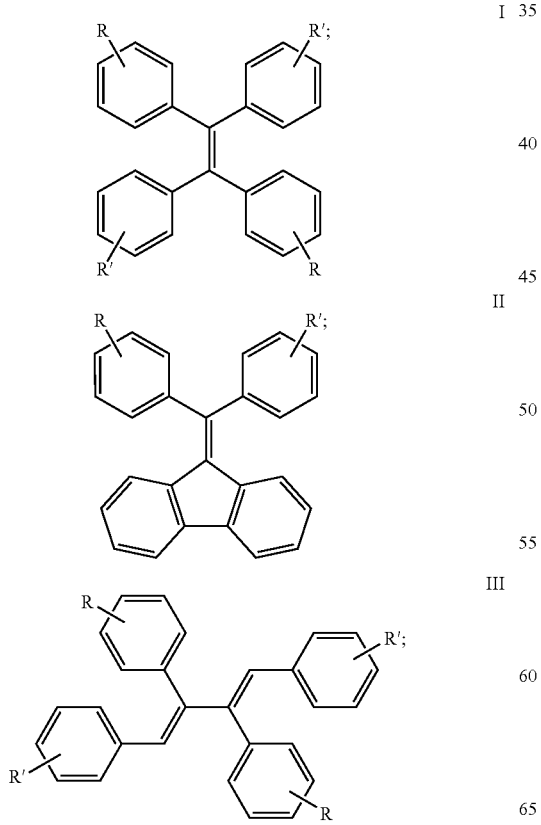

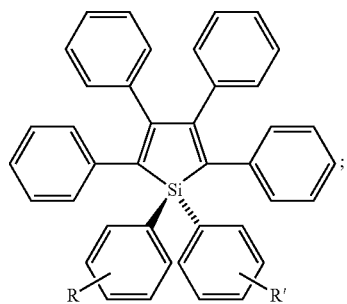

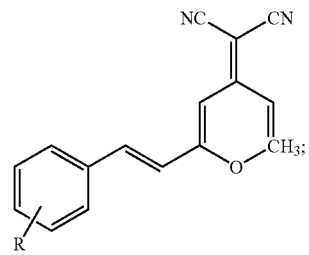

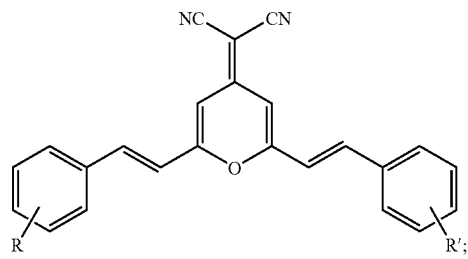

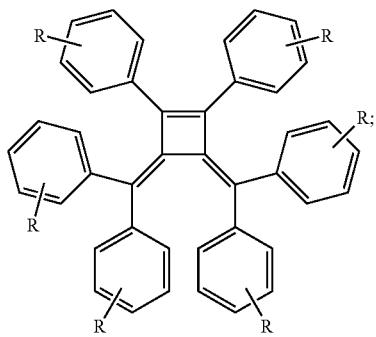

Cyclobutene

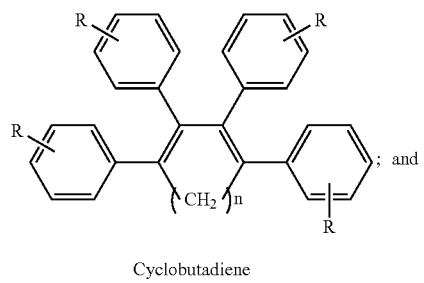

; and

Cyclobutadiene

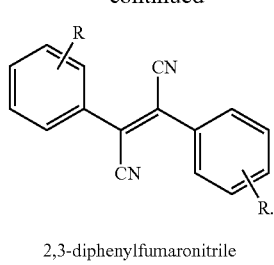

2,3-diphenylfumaronitrile wherein
R and R' are independently selected from H, X, B(OH)$_2$, (X)$_n$COOR'', (X)$_n$COOH, (X)$_n$NH$_2$, (X)$_n$NHR'', (X)$_n$NR''$_2$, (X)$_n$N+R''$_3$Br$^-$, (X)$_n$OH, (X)$_n$SH, (X)$_n$SO$_3^-$Na$^+$,

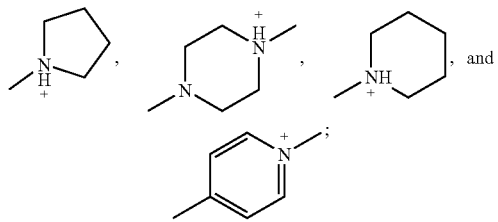

X is selected from (CH$_2$)$_n$, O(CH$_2$)$_n$, NH(CH$_2$)$_n$, N[(CH$_2$)$_n$]$_2$, and (OCH$_2$CH$_2$)$_n$; and R'' is selected from R, R', (CH$_2$)$_n$CH$_3$, CONH—X—, COO—X—, C$_6$H$_5$—R, —CH$_2$—C$_6$H$_5$, and C$_6$H$_5$;

and wherein n=0 to 20, and the compound is water-soluble and exhibits aggregation induced emission.

In another embodiment, the present subject matter relates to a water-soluble conjugated polyene compound, wherein the molecule has a backbone structure of a formula I.

In an embodiment, the present subject matter relates to a water-soluble conjugated polyene compound of claim formula I, wherein R is H and R' is selected from the group consisting of H, OH, COOH, CH$_2$NH$_2$, B(OH)$_2$, O(CH$_2$)$_3$SO$_3^-$Na$^+$, O(CH$_2$)$_2$N$^+$(CH$_2$CH$_3$)$_3$Br$^-$, O(CH$_2$)$_4$N$^+$(CH$_2$CH$_3$)$_3$Br$^-$, and N$^+$OCH$_3$.

In a further embodiment, the present subject matter relates to a water-soluble conjugated polyene compound of formula I, wherein R and R' are the same and are selected from the group consisting of OH, O(CH$_2$)$_2$N$^+$(CH$_2$CH$_3$)$_3$Br$^-$, and O(CH$_2$)$_4$N$^+$(CH$_2$CH$_3$)$_3$Br$^-$.

The presently described subject matter is also directed to a water-soluble conjugated polyene compound of formula I, selected from the group consisting of
1,2-Bis(4-hydroxyphenyl)-1,2-diphenylethylene;
1,2-Bis(4-methoxyphenyl)-1,2-diphenylethylene;
1,2-diphenyl-1,2-bis(4,4'-(3-sulfonato)propoxyl)phenylethylene;
N,N'-[1,2-diphenyl-1,2-bis(1,4-phenoxyethyl)vinyl]bis(triethylammonium bromide);
N,N'-[1,2-diphenyl-1,2-bis(1,4-phenoxybutyl)vinyl]bis(triethylammonium bromide);
1,1,2,2-tetrakis(4-hydroxyphenyl)ethylene;
N,N',N'',N'''-[1,2-tetrakis(1,4-phenoxybutyl)vinyl]tetrakis(triethylammonium bromide);
N,N',N'',N'''-[1,2-tetrakis(1,4-phenoxyethyl)vinyl]tetrakis(triethylammonium bromide);
4,4'-(1,2-diphenylvinyl)di(phenylboronic acid);
4,4'-(1,2-diphenylvinyl)di(phenylcarboxylic acid); and
1,2-di[4-(aminomethyl)phenyl]-1,2-diphenylethylene.

In another embodiment, the present subject matter relates to a water-soluble conjugated polyene compound wherein the molecule has a backbone structure of formula II.

In yet another embodiment, the present subject matter relates to a water-soluble conjugated polyene compound wherein the molecule has a backbone structure of formula III.

In a further embodiment, the present subject matter relates to a water-soluble conjugated polyene compound wherein the molecule has a backbone structure of formula IV.

In an embodiment, the present subject matter relates to a water-soluble conjugated polyene compound of formula IV, wherein R is H and R' is selected from the group consisting of CH$_2$N$^+$(CH$_2$CH$_3$)$_2$Br$^-$ and CH$_2$N(CH$_2$CH$_3$)$_2$. In another embodiment, the present subject matter relates to a water-soluble conjugated polyene compound of formula IV, selected from the group consisting of
1,1'-Bis-[4-(N,N'-diethylaminomethyl)phenyl]-2,3,4,5-tetraphenylsilole; and
N,N'-[1,1'-bis(1,4-benzylene)-2,3,4,5-tetraphenylsilolyl)bis(triethylammonium bromide).

In yet another embodiment, the present subject matter relates to a water-soluble conjugated polyene compound, wherein the molecule has a backbone structure of formula V.

In a further embodiment, the present subject matter relates to a water-soluble conjugated polyene compound, wherein the molecule has a backbone structure of formula VI.

In an embodiment, the present subject matter relates to a water-soluble conjugated polyene compound, wherein the compound does not exhibit aggregation induced quenching.

In an additional embodiment, the present subject matter relates to a method for detecting the presence or absence of a target biomacromolecule in a biological sample, comprising contacting the biological sample with the water-soluble conjugated polyene compound, and detecting luminescence.

In a further embodiment, the present subject matter relates to a method for detecting the presence or absence of a target biomacromolecule in a biological sample, wherein the biological sample is selected from the group consisting of a tissue sample, a cell sample, blood, saliva, spinal fluid, lymph fluid, vaginal fluid, seminal fluid, and urine.

In an embodiment, the present subject matter relates to a sensor device for detecting the presence or absence of a target biomacromolecule, comprising a holder and a detecting molecule comprising the water-soluble conjugated polyene compound, the detecting molecule being held in place by the holder and being accessible to the target molecule or substance.

In a further embodiment, the present subject matter relates to a sensor device, wherein the luminance of the detecting molecule increases upon contact with the target biomacromolecule.

In another embodiment, the present subject matter relates to a sensor device, wherein the holder is a container and the detecting molecule is disposed inside the container; the container having one or more openings or orifices to allow access to the detecting molecule by the target molecule.

In yet another embodiment, the present subject matter relates to a sensor device, wherein the holder is a surface on which the detecting molecule is coated in a thin film.

In an embodiment, the present subject matter relates to water-dispersible, fluorescent, polymeric particles, comprising or consisting of a water-soluble conjugated polyene compound of formula VII; and a polymer comprising one or more ethylenically unsaturated monomers.

In a further embodiment, the present subject matter relates to water-dispersible, fluorescent, polymeric particles, wherein R is H and R' is selected from H, OH, COOH, and NH$_2$.

In yet a further embodiment, the present subject matter relates to water-dispersible, fluorescent, polymeric particles, wherein the water-soluble conjugated polyene compound is selected from the group consisting of
4,4'-(1,2-diphenylvinyl)di(phenylcarboxylic acid);
1,2-Bis(4-methoxyphenyl)-1,2-diphenylethylene; and
1,2-Bis(4-hydroxyphenyl)-1,2-diphenylethylene.

In another embodiment, the present subject matter relates to water-dispersible, fluorescent, polymeric particles, wherein the polymer is a homopolymer or a copolymer comprising one or more monomers selected from the group consisting of a vinylaromatic monomer, an ethylenic monomer, an alkanoic acid or ester or anhydride, and an ethylchic acid or ester, wherein one or more of the one or more monomers is optionally functionalized.

In a further embodiment, the present subject matter relates to water-dispersible, fluorescent, polymeric particles, comprising at least one functionalized monomer.

In another embodiment, the present subject matter relates to water-dispersible, fluorescent, polymeric particles, wherein the ethylenic monomer is selected from an ethylenic monomer of isoprene, 1,3-butadiene, vinylidene chloride, or acrylonitrile; the vinylaromatic monomer is selected from styrene, bromo-styrene, α-methylstyrene, ethylstyrene, vinyl-toluene, chlorostyrene, chloromethylstyrene, or vinyl-naphthalene; the alkanoic acid or ester or anhydride is selected from acrylic acid, methacrylic acid, an alkyl acrylate or an alkyl methacrylate in which the alkyl group possess from 3 to 10 carbon atoms; an hydroxyalkyl acrylate, acrylamide, ethylenic acid ester containing 4 or 5 carbon atoms; or a difunctional monomer selected from divinylbenzene or 2,2-dimethyl-1,3-propylene diacrylate.

In yet a further embodiment, the present subject matter relates to water-dispersible, fluorescent, polymeric particles, wherein the one or more monomers are selected from the group consisting of styrene, methyl methacrylate, ethyl acrylate, butyl acrylate, 2-hydroxyethyl methacrylate, acrylic acid, and acrylamide.

In an embodiment, the present subject matter relates to water-dispersible, fluorescent, polymeric particles, wherein the at least one functionalized monomer is selected from the group consisting of 2-hydroxyethyl methacrylate, 2-aminoethyl methacrylate, trimethylammoniumethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein, and glutaraldehyde.

In a further embodiment, the present subject matter relates to water-dispersible, fluorescent, polymeric particles, wherein the one or more ethylenically unsaturated monomers comprise or consist of methyl methacrylate, butyl acrylate and 2-hydroxyethyl methacrylate.

In another embodiment, the present subject matter relates to water-dispersible, fluorescent, polymeric particles, wherein the methyl methacrylate, butyl acrylate, and 2-hydroxyethyl methacrylate are present in a ratio of from 4:5:1 to 5:4:1.

In yet another embodiment, the present subject matter relates to water-dispersible, fluorescent, polymeric particles, wherein the one or more ethylenically unsaturated monomers comprise or consist of methyl methacrylate, butyl acrylate, and acrylic acid and/or acrylamide.

In a further embodiment, the present subject matter relates to water-dispersible, fluorescent, polymeric particles, wherein the ratio of monomer to functionalized monomer is in the range of from about 3:1 to about 20:1.

In another embodiment, the present subject matter relates to water-dispersible, fluorescent, polymeric particles, wherein the ratio of monomer to functionalized monomer is in the range of from about 7:1 to about 11:1.

In yet another embodiment, the present subject matter relates to water-dispersible, fluorescent, polymeric particles, wherein the ratio of monomer to functionalized monomer is about 9:1.

In an embodiment, the present subject matter relates to water-dispersible, fluorescent, polymeric particles, having a glass transition temperature below room temperature.

In a further embodiment, the present subject matter relates to water-dispersible, fluorescent, polymeric particles, comprising microparticles.

In yet a further embodiment, the present subject matter relates to water-dispersible, fluorescent, polymeric particles, wherein the microparticles comprise a mean particle diameter in the range of from about 0.01 µm to about 5 µm.

In another embodiment, the present subject matter relates to water-dispersible, fluorescent, polymeric particles, wherein the microparticles comprise a mean particle diameter in the range of from about 10 nm to about 500 nm.

In an embodiment, the present subject matter relates to water-dispersible, fluorescent, polymeric particles, wherein greater than about 50% of the microparticles comprise a mean particle diameter in the range of from about 10 nm to about 500 nm.

In a further embodiment, the present subject matter relates to water-dispersible, fluorescent, polymeric particles, wherein greater than about 70% of the microparticles comprise a mean particle diameter in the range of from about 40 nm to about 400 nm.

In yet a further embodiment, the present subject matter relates to a method for making water-dispersible, fluorescent, polymeric particles, comprising or consisting of: dissolving the water-soluble conjugated polyene compound in the one or more monomers to form a monomer solution; providing an aqueous composition comprising one or more members selected from the group consisting of a surfactant, a stabilizer and a cross-linking agent; adding the monomer solution dropwise to the aqueous composition to form a mixture; and polymerizing the mixture to produce the water-dispersible, fluorescent, polymeric particles.

In another embodiment, the present subject matter relates to the method for making water-dispersible, fluorescent, polymeric particles, wherein polymerizing comprises emulsion polymerization, microemulsion polymerization, suspension polymerization, or dispersion polymerization.

In another embodiment, the present subject matter relates to the method for making water-dispersible, fluorescent, polymeric particles, wherein the water-dispersible, fluorescent, polymeric particles are dispersed stably in the aqueous composition.

In a further embodiment, the present subject matter relates to the water-dispersible, fluorescent, polymeric particles, comprising a formulation selected from a bioprobe, a coating, a paint, a flexible free-standing film, a cosmetic, a fluidic tracer, or a marker. A fluidic tracer can be used to investigate capillary flow, to define neuronal cell connectivity and to study dye translocation through gap junctions, as well as to follow cell division, cell lysis or liposome fusion. A marker can be used as an indicator of a biologic state, fore example, pH, polarity, and viscosity of the biological environment.

In another embodiment, the present subject matter relates a flexible free-standing film comprising water-dispersible, fluorescent, polymeric particles.

BRIEF DESCRIPTION OF DRAWINGS

FIG. 1A-C shows that the three TPE derivatives are practically nonemissive when dissolved but highly emissive when aggregated.

FIG. 6A illustrates the emission spectra of TPE-C4N$^+$ (4) (2.5 µM) in an aqueous phosphate buffer (pH=7) and in the buffers containing 300 µg/ml calf thymus DNA ("ctDNA") and 500 µg/ml BSA. FIG. 6B illustrates plots of fluorescence intensities of buffer solutions of TPE-C4N$^+$ (4) at 463 nm versus concentrations of ct DNA and BSA. FIGS. 5 and 6 illustrate that the FL of cationic TPE derivatives in aqueous solution can is turned on in the presence of BSA or DNA. TPE-C2N$^+$ exhibits better affinity to ctDNA than BSA while TPE-C4N$^+$ gives the opposite result.

FIG. 9 illustrates that N+C2-TPE-C2N+ has larger affinity to DNA than to RNA and proteins.

FIG. 12A illustrates the emission spectra of derivative 4 (2.5 µM) in an aqueous phosphate buffer (pH=7) and in the buffers containing 300 µg ml$^{-1}$ ct DNA and 500 µg ml$^{-1}$ BSA.

FIG. 12B illustrates plots of fluorescence intensities of buffer solutions of derivative 4 at 463 nm vs. concentrations of ct DNA and BSA.

FIG. 13A illustrates the absorption and emission spectra of derivative 4 (2.5 µM) in water and a glycerol-water mixture at 25° C.

FIG. 13B illustrates the emission spectra of derivative 4 (2.5 µM)

DETAILED DESCRIPTION OF PARTICULAR EMBODIMENTS

Definitions

Figures 1A, 1B, 1C:
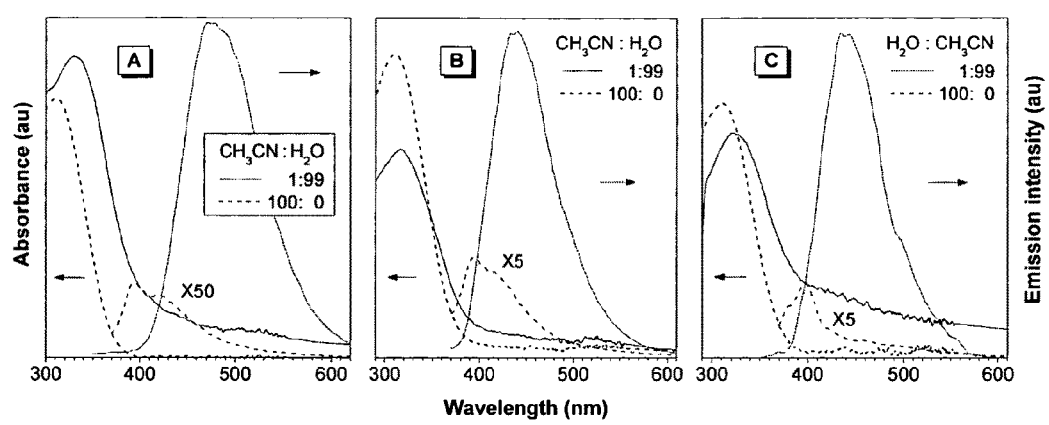
FIGS. 1A, 1B, and 1C illustrate absorption and emission spectra of (A) TPE-OMe (10 µM), (B) TPE-OH (10 µM), and (C) TPE-SO3 (5 µM) in pure acetonitrile, pure water, and mixtures of acetonitrile and water.
Figures 2A, 2B, 2C:
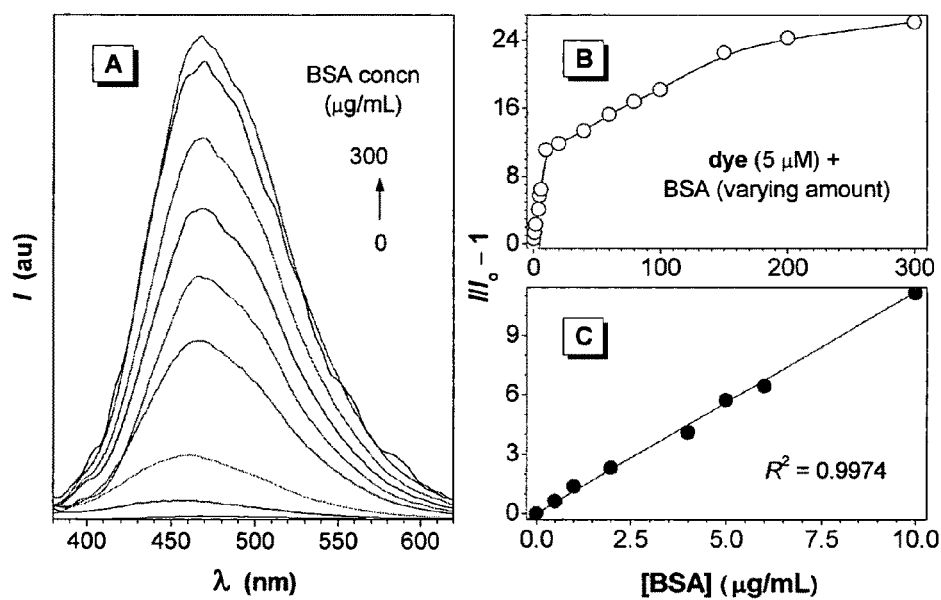
FIG. 2A illustrates the change of fluorescence spectrum of TPE-OH.Na2 (5 µM) with addition of BSA in aqueous phosphate buffer (pH=7.0).
FIG. 2B illustrates a plot of fluorescence intensity at 476 nm versus BSA concentration.
FIG. 2C illustrates the linear region of the binding isotherm of TPE-OH to BSA. The FL of TPE-OH is turned on in the presence of BSA (FIG. 2). Its intensity increased with increasing BSA concentration, and in the BSA concentration range of 0-10 µg/ml exhibited a linear relationship with a $R^2$ value of 0.9974.
Figures 3A, 3B, 3C:
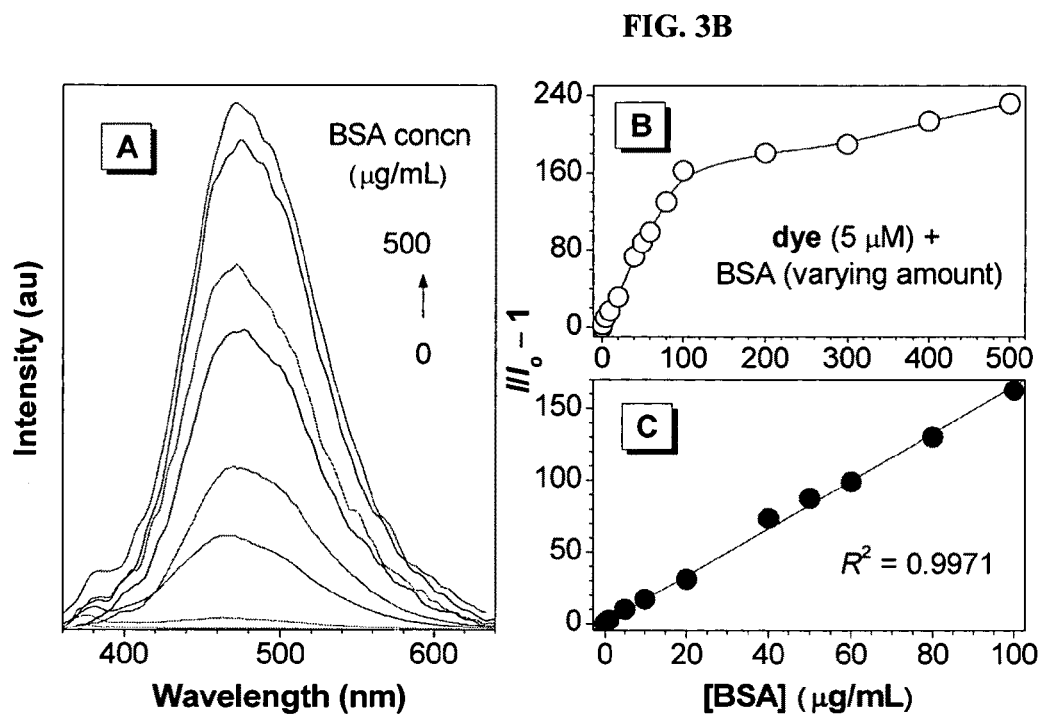
FIG. 3A illustrates the change of FL spectrum of TPE-SO3 with addition of BSA in an aqueous phosphate buffer.
FIG. 3B illustrates the plot of FL intensity at 472 nm versus BSA concentration.
FIG. 3C illustrates the linear region of the $(I/I_0-1)$-[BSA] plot in FIG. 3B. TPE-SO3 shows similar behavior as TPE-OH but better performance. The FL intensity increase up to 240 times upon binding with BSA. Linear range in the BSA concentration from 0 to 100 µg/ml is given with a $R^2$ value of 0.9971.
Figures 4A, 4B:
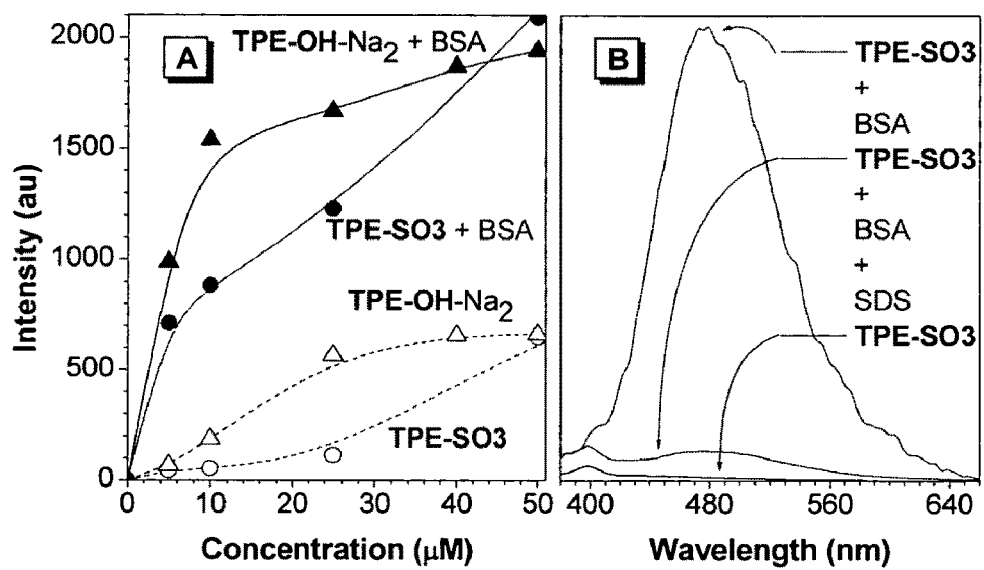
FIG. 4A illustrates the effect of dye concentration on the FL intensity of buffer solution of TPE-OH.Na2 at 467 nm or TPE-SO3 at 472 nm in the absence or presence of BSA (10 µg/ml).
FIG. 4B illustrates the effect of BSA (100 µg/ml) and/or SDS (1 mg/ml) on the FL spectrum of a buffer solution of TPE-SO3 (5 µM). Conventional fluorescent dyes suffer from self-quenching at high dye concentrations, whereas the FL of the AIE-active dyes is intensified with increasing dye concentration as illustrated in FIG. 4A. The FL of TPE-SO3 solution in the presence of BSA is diminished by adding surfactants such as sodium dodecyl sulphate (SDS) in high concentration (1 mg/ml) as illustrated in FIG. 4B.
Figure 5A:
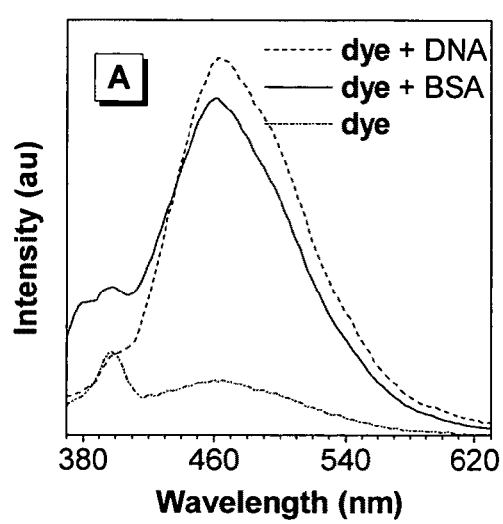
FIG. 5A illustrates the emission spectra of TPE-C2N$^+$ (2.5 µM) in an aqueous phosphate buffer (pH=7) and in the buffers containing 300 µg/ml BSA.
Figure 5B:
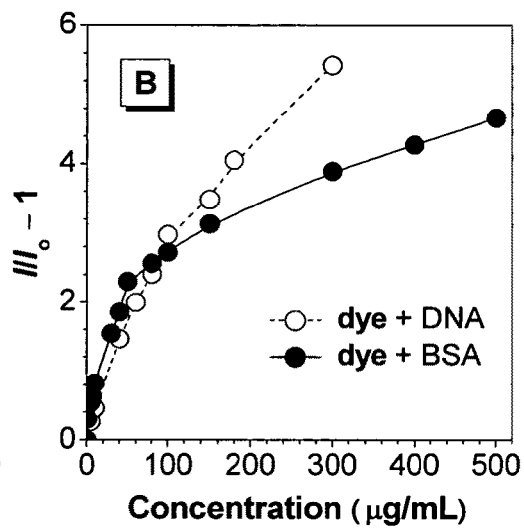
FIG. 5B illustrates a plot of fluorescence intensities of buffer solutions of TPE-C2N$^+$ at 462 nm versus concentrations of DNA and BSA.
Figure 7A:
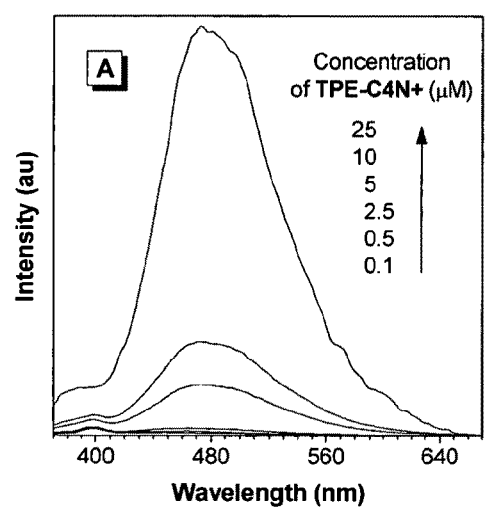
FIG. 7A illustrates the emission spectra of TPE-C4N+ (2.5 µM) in an aqueous phosphate buffer (pH=7) and in buffers containing 300 µg/ml ctDNA and 500 µg/ml BSA.
Figure 7B:
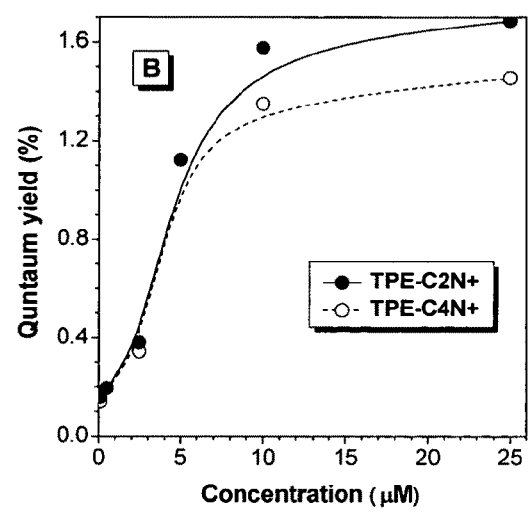
FIG. 7B illustrates plots of fluorescence intensities of buffer solutions of TPE-C4N+ at 463 nm versus concentrations of ctDNA and BSA. The FL of TPE-C4N+ and TPE-C2N+ is intensified with increased dye concentration.
Figure 8:
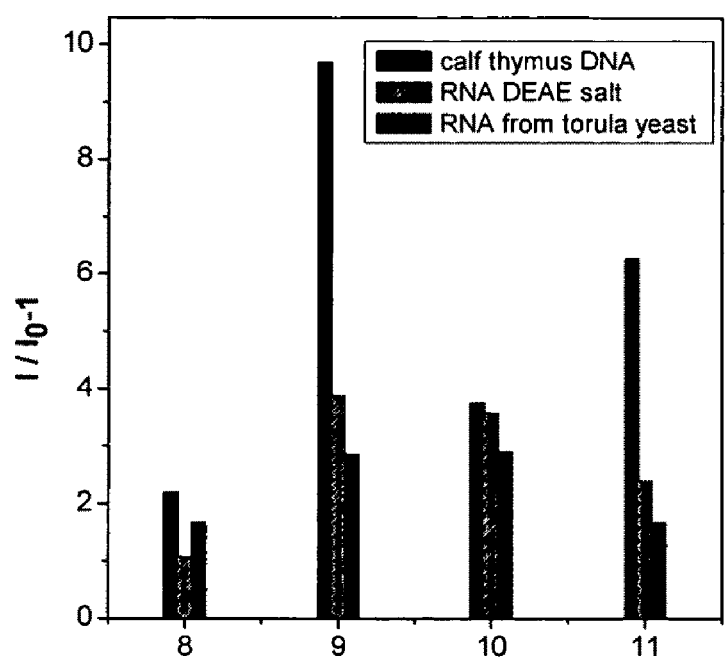
FIG. 8 illustrates increments of fluorescence of TPE-C2N+ (8), N+C2-TPE-C2N+ (9), TPE-C4N+ (10), N+C4-TPE-C4N+ (11) when binding with 10 µg/ml ctDNA/10 µg/ml RNA diethylaminoethanol (DEAE) salt from torula yeast/10 µg/ml RNA from torula yeast in buffer solution pH=7. Concentration of dyes: 5 µM; excitation wavelength: 350 nm. The four cationic TPE derivatives display larger FL enhancement in the presence of DNA than that of RNA. Meanwhile N+C2-TPE-C2N+ and N+C4-TPE-C4N+ show much larger variety of FL than that of TPE-C2N+ and TPE-C4N+ in the presence of DNA and RNA.
Figure 9:
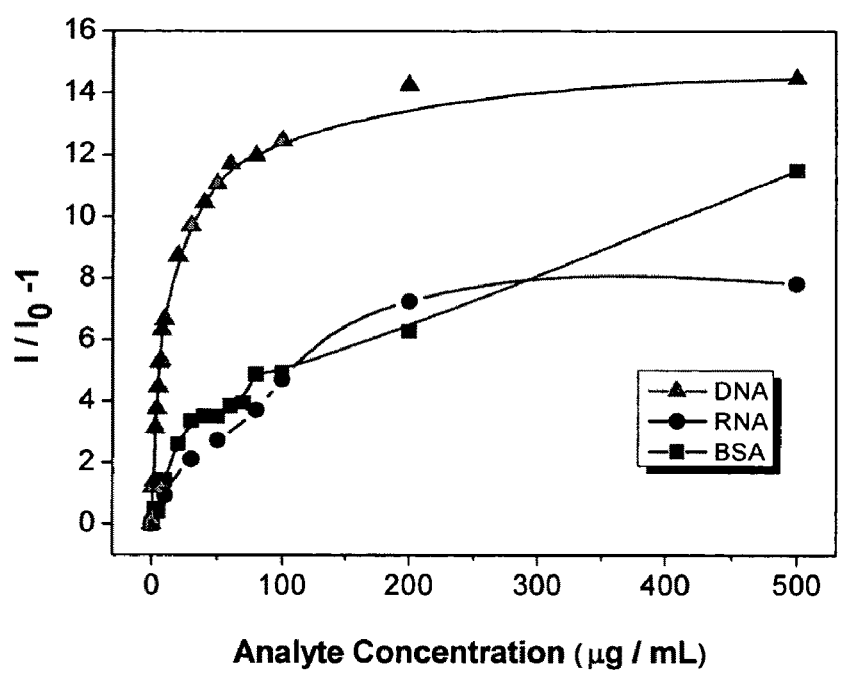
FIG. 9 illustrates the binding isotherm of N+C2-TPE-C2N+ (5 µM) to ctDNA/RNA from torula yeast/BSA (plot of the fluorescence intensity at 470 nm for ctDNA/RNA, and at 467 nm for BSA) in aqueous phosphate buffer (pH=7.0).
Figure 10:
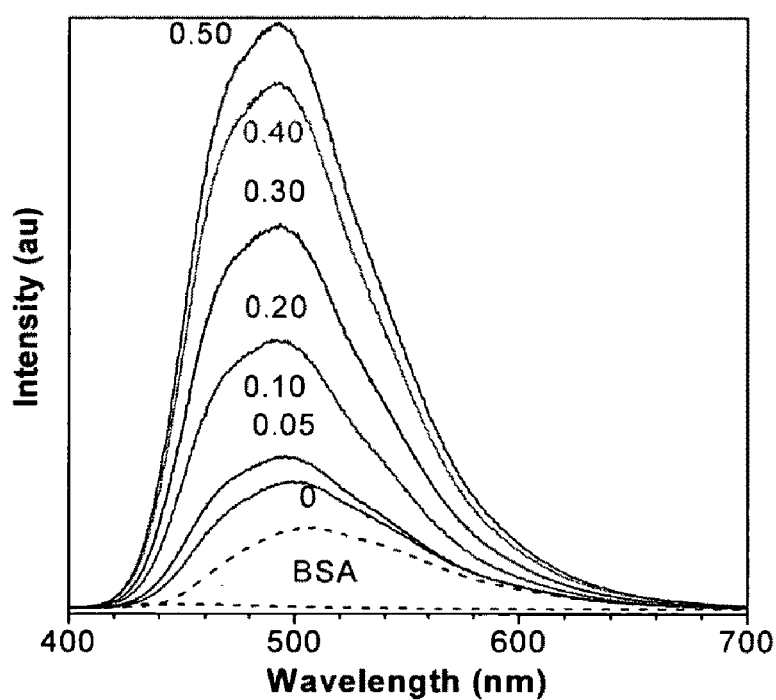
FIG. 10 illustrates the photoluminescence spectra of the water/methanol (6:4) solutions of a PPS-OH ($5.7 \times 10^{-5}$ M) in the presence of KOH ($8.4 \times 10^{-4}$ M) and BSA. The spectrum of a "pure" BSA solution (0.50 wt %) is shown for comparison. Excitation wavelength: 378 nm. Water-soluble silole derivatives also show this "turn-on" property when binding to BSA in aqueous solutions.

The following definitions are provided for the purpose of understanding the present invention and for constructing the appended patent claims.

It is noted that, as used in this specification and the appended claims, the singular forms "a," "an" and "the" include plural references unless the context clearly dictates otherwise.

"A chemically conjugated system" means a system of atoms covalently bonded with alternating single and double bonds in a molecule of an organic compound.

"A polyene" means a molecule of an organic compound containing more than one alkene. For example, a diene has two C═C; a triene has three C═C; etc.

"Target molecule" means the molecule whose changes in concentration in an environment are intended to be detected by a sensor. A target molecule can comprise or consist of a biomacromolecule. "Detecting molecule" means a molecule which, upon contacting with a target molecule in the environment, can provide a signal perceivable to human.

"Alkyl" means, unless otherwise specified, an aliphatic hydrocarbon group which may be straight or branched chain having about 1 to about 15 carbon atoms in the chain, optionally substituted by one or more halogen atoms. A particularly suitable alkyl group has from 1 to about 6 carbon atoms. The term "unsaturated" refers to the presence of one or more double and triple bonds between atoms of a radical group, for example.

"Heteroatom" means an atom selected from the group consisting nitrogen, oxygen, sulfur, phosphorus, boron and silicon.

"Heteroaryl" as a group or part of a group denotes an optionally substituted aromatic monocyclic or multicyclic organic moiety of about 5 to about 10 ring members in which at least one ring member is a heteroatom.

"Cycloalkyl" means an optionally substituted non-aromatic monocyclic or multicyclic ring system of about 3 to about 10 carbon atoms.

"Heterocycloalkyl" means a cycloalkyl group of about 3 to 7 ring members in which at least one ring member is a heteroatom.

"Aryl" as a group or part of a group denotes an optionally substituted monocyclic or multicyclic aromatic carbocyclic moiety of about 6 to about 14 carbon atoms, such as phenyl or naphthyl.

"Heteroalkyl" refer to alkyl in which at least one carbon atom is replaced by a heteroatom.

"Biomacromolecule" means a high molecular biological weight substance comprising or consisting of one or more of nucleic acids, proteins and/or complex carbohydrates.

"Microparticle" means any microscopic particle or particle population having a mean diameter of less than about 10 microns (em); less than about 5 µm; less than about 1 µm; or having a mean diameter in the range of from greater than or equal to 10 nm to less than 5 µm; of from greater than or equal to 40 nm to less than 3 µm; of from greater than or equal to 50 nm to less than 1 µm; of from greater than or equal to 60 nm to less than 750 nm; of from greater than or equal to 60 nm to less than 500 nm; of from greater than or equal to 60 nm to less than 300 nm; of from greater than or equal to 80 nm to less than or equal to 250 nm; of from greater than or equal to 1 µm to less than 10 µm; of from greater than or equal to 2.5 µm to less than 10 µm; of from greater than or equal to 5 µm to less than 10 µm; of from greater than or equal to 7.5 µm to less than 10 µm; of from greater than or equal to 2.5 µm to 7.5 µm; or having a mean diameter in the range of from greater than or equal to 5 µm to 7.5 µm. In an embodiment, greater than 99% of the microparticles of a microparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 20% of the microparticles have a mean diameter falling within a described range; or greater than about 10% of the microparticles have a mean diameter falling within a described range.

"Nanoparticle" means any microscopic particle or particle population having a mean diameter of less than about 100 nanometers (nm); less than about 90 nm; less than about 80 nm; less than about 70 nm; less than about 60 nm; less than about 50 nm in diameter; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 to 80 nm; or having a mean diameter of from 30 to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 20% of the microparticles have a mean diameter falling within a described range; or greater than about 10% of the microparticles have a mean diameter falling within a described range.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Water-Soluble Conjugated Polyenes

Examples of water-soluble conjugated polyene functional AIE-active compounds

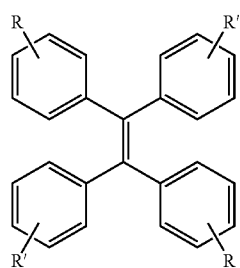

Tetraphenylethylene

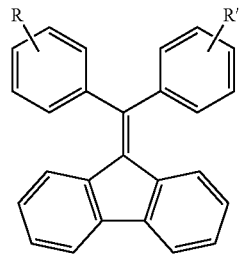

Fulvene

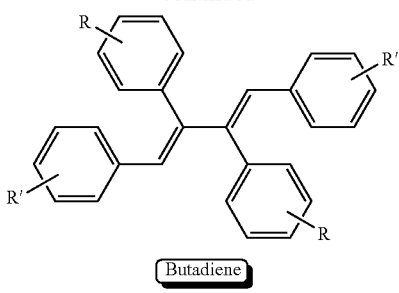

Butadiene

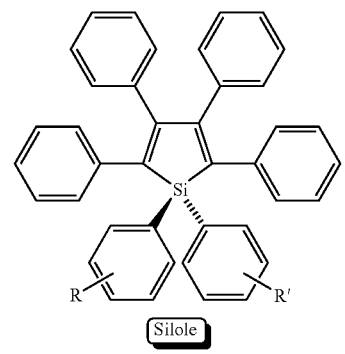

Silole

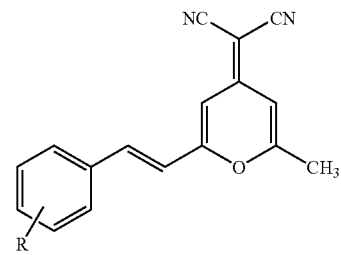

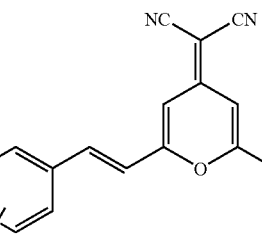

Pyran

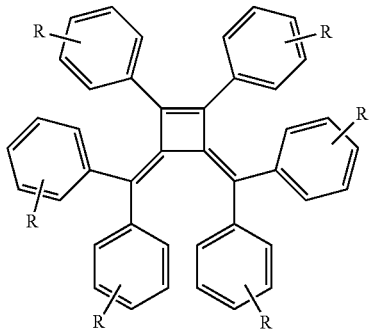

Cyclobutene

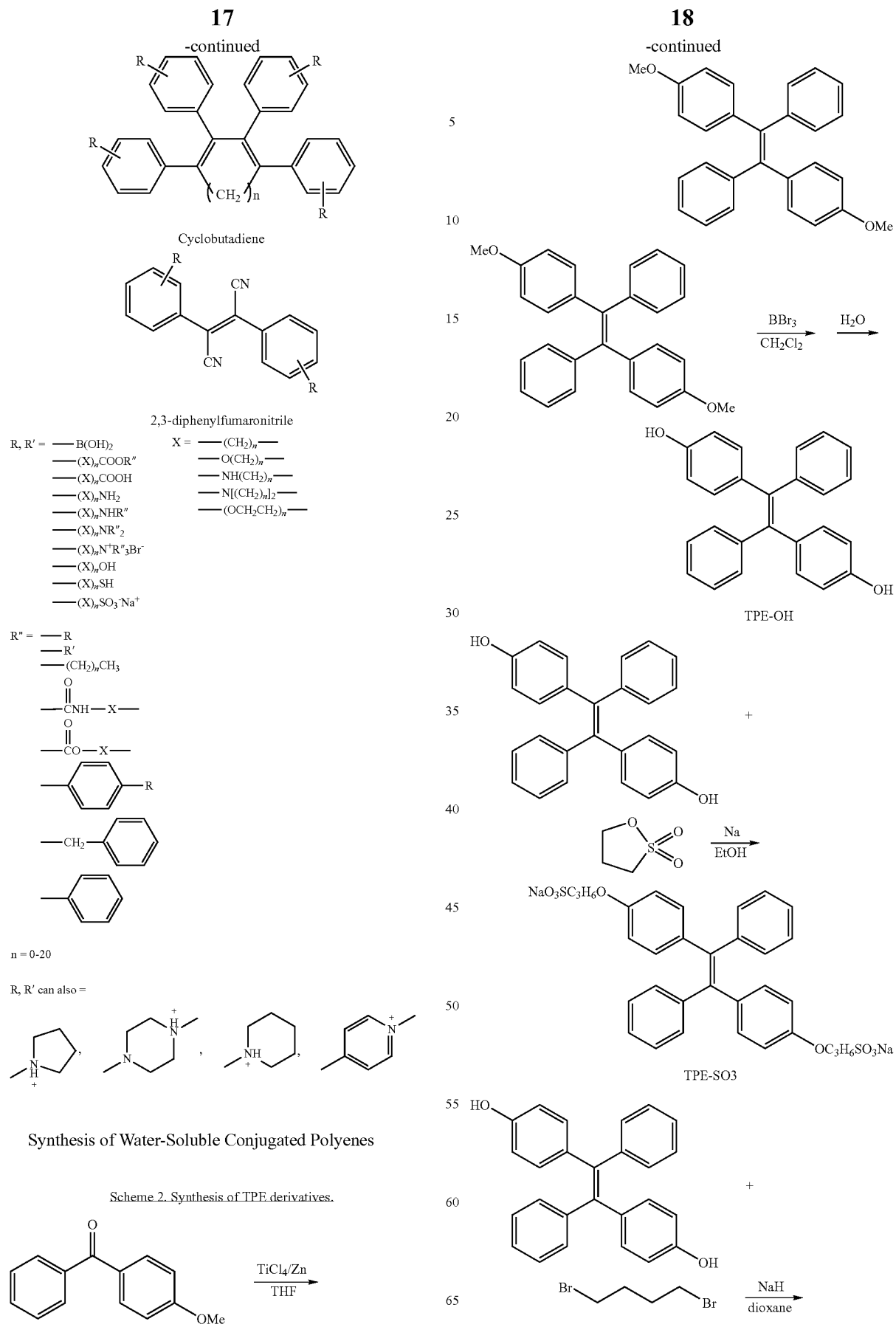

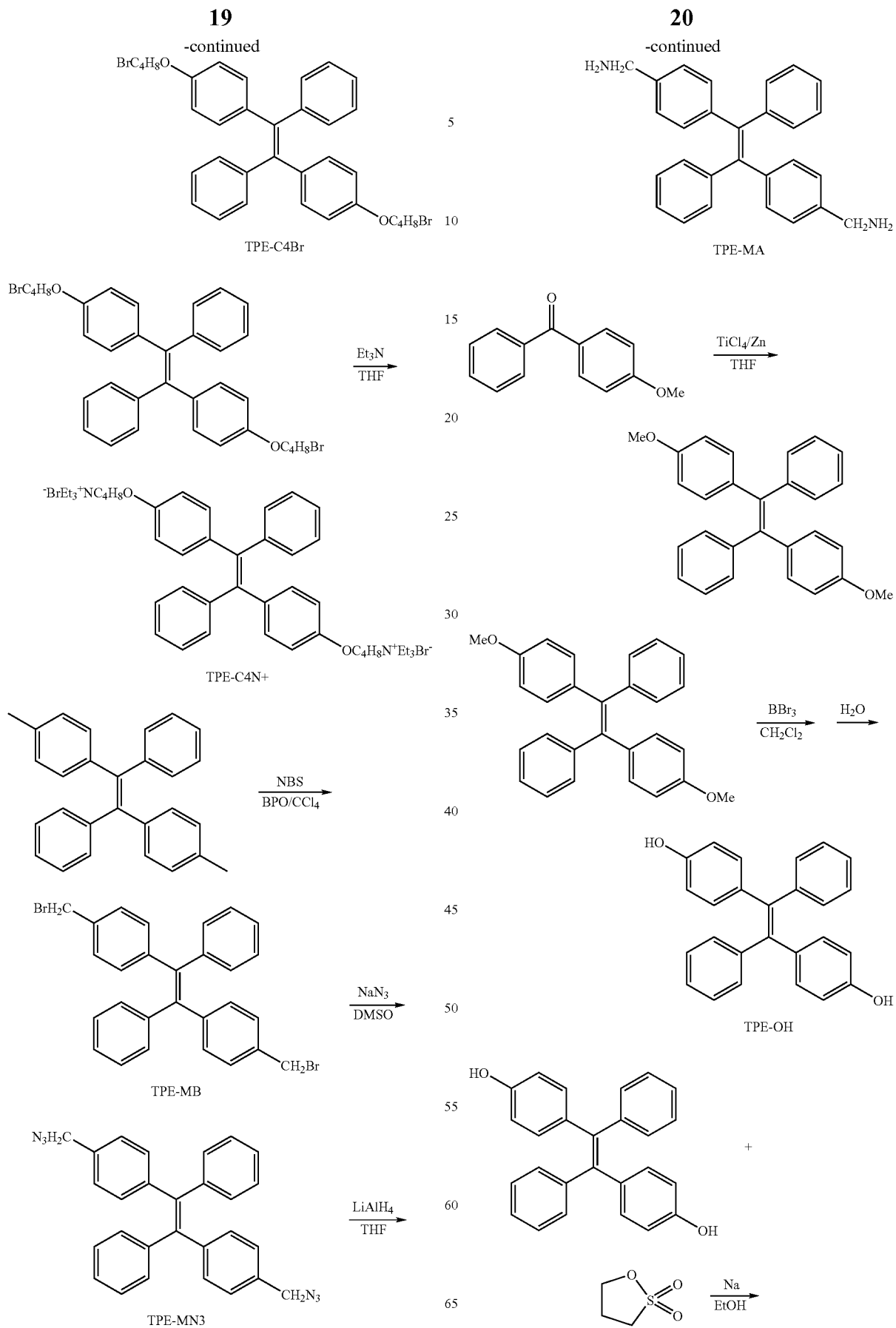

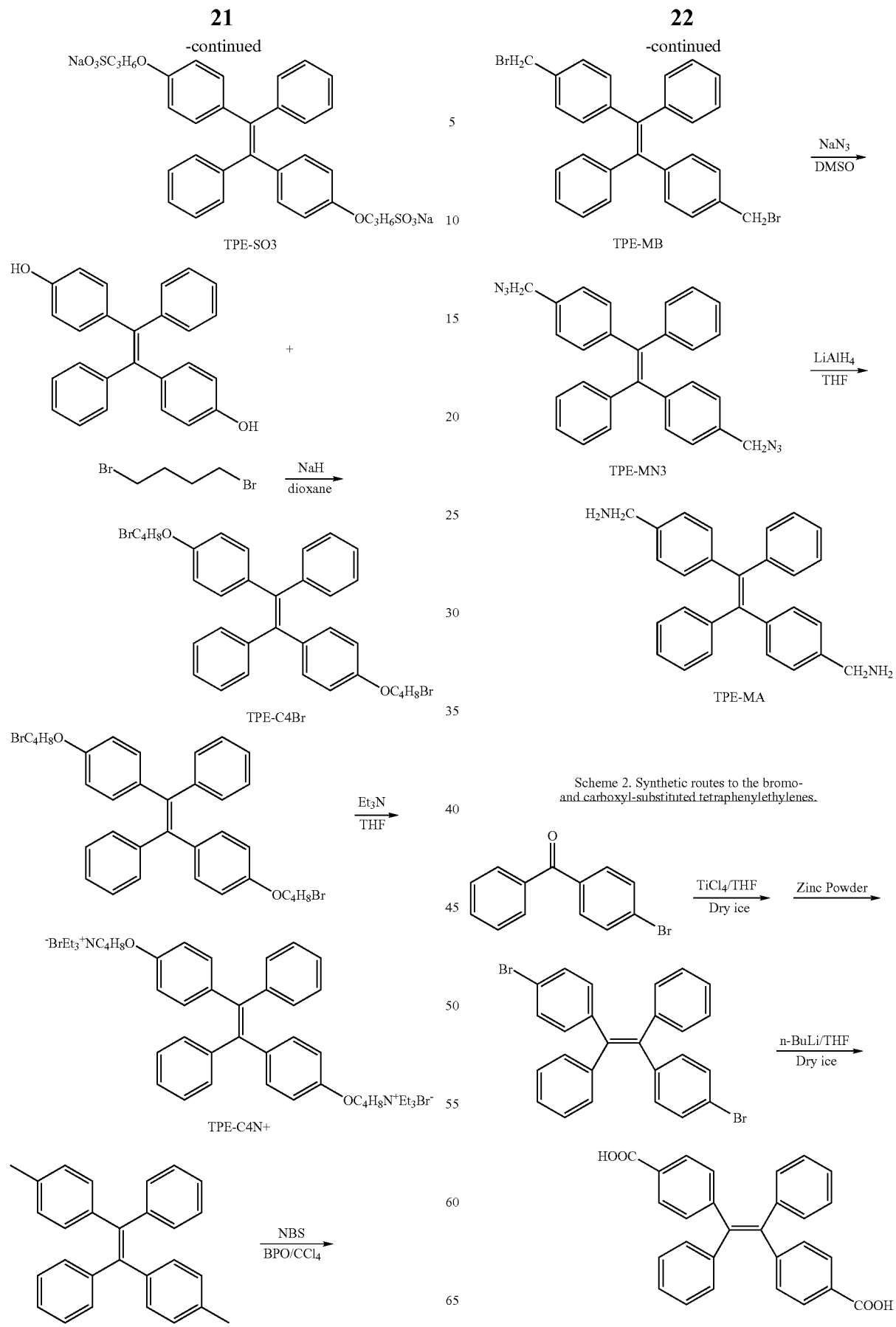

Scheme 3. Synthesis of silole derivatives.
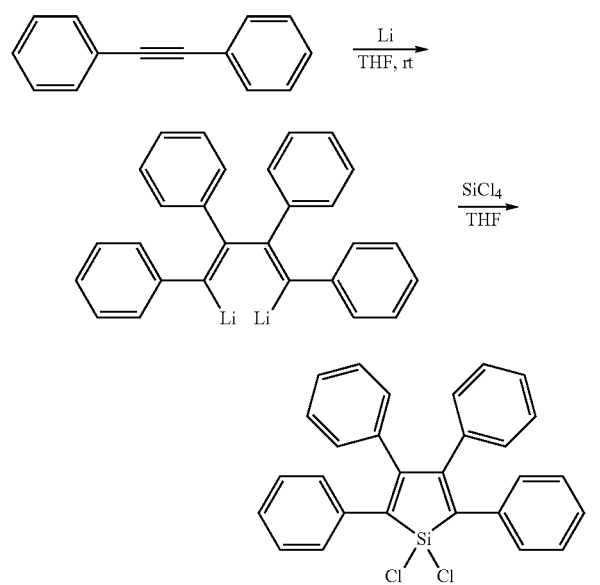
Scheme 4. Synthesis of Butadiene and Cyclobutadiene Derivatives
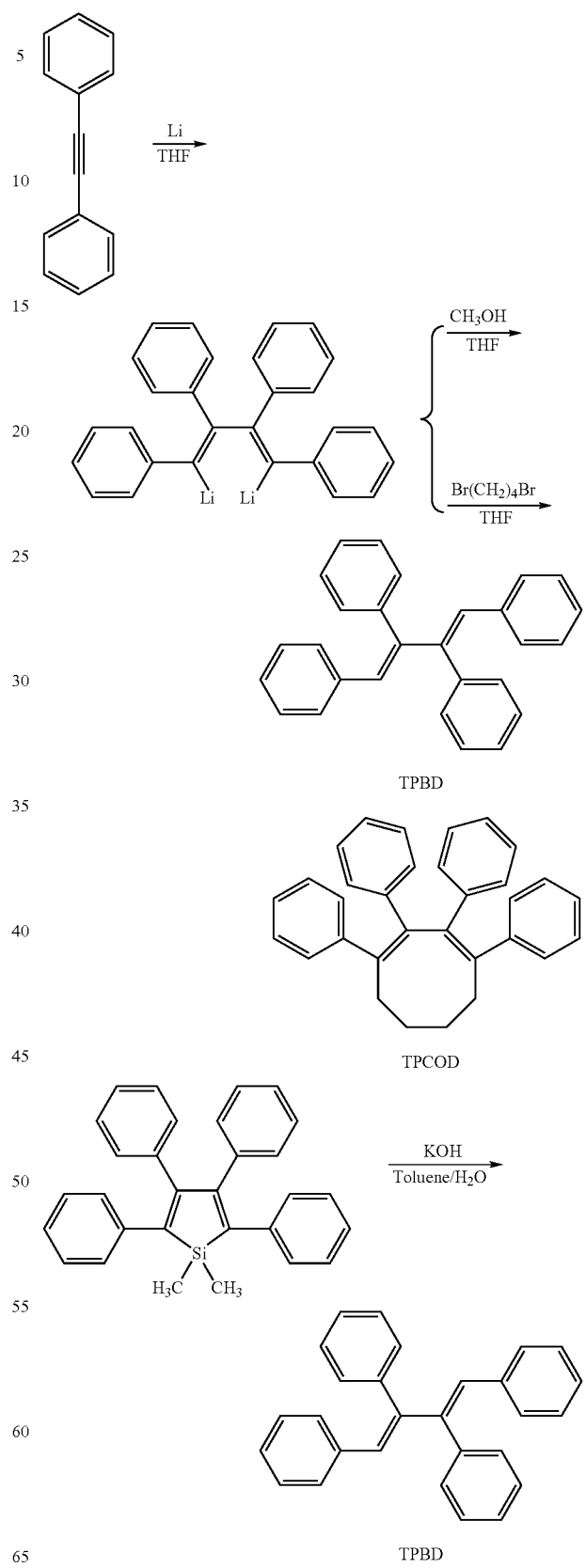

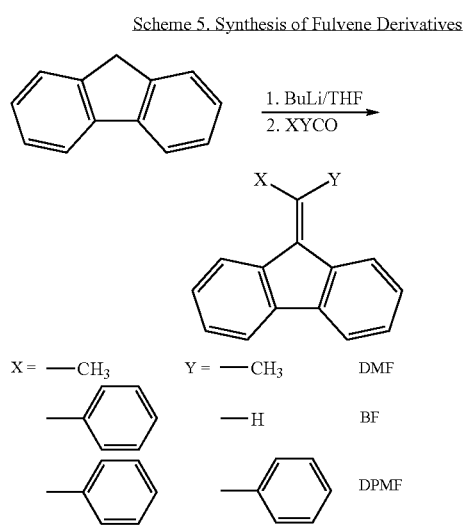

Scheme 5. Synthesis of Fulvene Derivatives

| X = | Y = | |
|---|---|---|
| —CH₃ | —CH₃ | DMF |
| —C₆H₅ | —H | BF |
| —C₆H₅ | —C₆H₅ | DPMF |

Scheme 6. Synthesis of Diphenylethylene Derivatives

MPDPE

Appropriately substituted versions of the precursors illustrated in the above schemes can be readily selected and employed, by the person of ordinary skill in the art to which the presently described subject matter pertains, to synthesize corresponding substituted products without undue experimentation.

Fluorescent Polymer Particles

The presently described subject matter is directed to water-dispersible, fluorescent, polymeric particles, which comprise or consist of the presently described tetraphenylethylene (TPE)-derived water-soluble conjugated polyenes ("TPE dyes") that exhibit aggregation-induced-emission (AIE), and a variety of polymer matrices having desirable hydrophilicity and chemical composition that can be designed to proved desirable characteristics.

The presently described TPE-derived water-soluble conjugated polyenes, i.e., "TPE dyes," have conjugated molecular structures which can be expressed by the following formula:

wherein R is selected from H, X, B(OH)$_2$, (X)$_n$COOR", (X)$_n$COOH, (X)$_n$NH$_2$, (X)$_n$NHR", (X)$_n$NR"$_2$, (X)$_n$N+R"$_3$Br⁻, (X)$_n$OH, (X)$_n$SH, and (X)$_n$SO$_3$⁻Na⁺;

X is selected from (CH$_2$)$_n$, O(CH$_2$)$_n$, NH(CH$_2$)$_n$, N[(CH2)$_n$]$_2$, and (OCH$_2$CH$_2$)$_n$; and R" is selected from R, R', (CH$_2$)$_n$CH$_3$, CONH—X—, COO—X—, C$_6$H$_5$—R, —CH$_2$—C$_6$H$_5$, and C$_6$H$_5$; and wherein n=0 to 20.

In an embodiment, R is selected from H, OH, COOH, and NH$_2$.

The described TPE dyes possess unique characteristics, in that when molecularly dissolved in aqueous solutions, for example, water, emission is weak, whereas when aggregated in poor non-aqueous solvents or fabricated into thin films emission is substantially increased.

The TPE dyes can be prepared according to the synthetic routes shown in Scheme 2 described herein. Bromo-substituted TPE (TPE-Br) can first be prepared by the McMurry coupling reaction of 4-bromobenzophenone using titanium (IV) chloride/zinc as catalyst. Then the bromo groups in TPE-Br can be transformed into other groups, e.g., carboxyl functionalities, by reaction with n-butyl lithium followed by dry ice.

The polymers for encapsulation of the presently described TPE dyes are obtained by polymerization of ethylenically unsaturated monomers. Such a polymer can be a homopolymer or copolymer containing units derived from vinylaromatic or ethylenic monomers, or from alkanoic or ethylchic acids or esters, which are optionally functionalized. This type of polymer is readily accessible to any person skilled in the art and it will be sufficient to mention only a few such polymers below, in a non-limiting manner. Such polymers can comprise or consist of one or more of the following: ethylenic monomers of isoprene, 1,3-butadiene, vinylidene chloride or acrylonitrile type; vinylaromatic monomers such as styrene, bromo-styrene, alpha-methylstyrene, ethylstyrere, vinyltoluene, chlorostyrene or chloromethylstyrene, or vinylnaphthalene; alkanoic acids, esters or anhydrides such as acrylic acid, methacrylic acid, alkyl acrylates and alkyl methacrylates in which the alkyl group possesses 3 to 10 carbon atoms; hydroxyalkyl acrylates, acrylamides, ethylenic acid esters containing 4 or 5 carbon atoms; and difunctional monomers such as divinylbenzene or 2,2-dimethyl-1,3-propylene diacrylate and/or other copolymerizable monomers. Suitable monomers can comprise or consist of styrene, methyl methacrylate, ethyl acrylate, butyl acrylate, 2-hydroxyethyl methacrylate, acrylic acid, and acrylamide. These monomers are used alone or mixed with each other in any proportion, or alternatively mixed with another copolymerizable monomer selected from those described above. The functional groups can be incorporated onto the surface of the fluorescent particles by, for example, using a mixture of monomer and functionalized monomer during the polymerization. The functionalized monomer used can comprise or consist of one or more of the following: 2-hyroxyethyl methacrylate, 2-aminoethyl methacrylate, trimethylammoniumethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein, glutaraldehyde and the like.

The polymer particles may be formed by the use of appropriate polymerization techniques such as conventional emulsion polymerization, microemulsion polymerization, suspension polymerization or other means of polymerization with or without a crosslinking agent such as divinyl benzene or the like. These techniques and agents are well known to those of ordinary skill in the art to which the present invention pertains. The skilled artisan can readily select and employ such techniques and agents without undue experimentation.

The described TPE dyes are dissolved in the monomer(s) prior to polymerization, then incorporated into the polymer matrices through the particle formation process. TPE dyes are organic in nature, which makes them readily soluble in the monomers used. TPE dyes can also withstand common polymerization conditions. Further, TPE dyes, for example, having various peripheral substituent groups on the aromatic rings, have an affinity towards the interior of the particles. That is, they are chemically compatible with the polymers constituting the latex particles. This compatibility is important during the formation of the corresponding fluorescent polymer particles.

The fluorescent polymer particles prepared according to this invention are stable aqueous dispersions whose size is as described herein and is generally between 0.01 micron and 5 microns, for example, less than 1 micron in diameter, regardless of the polymer composition. The aqueous dispersions have a content of polymer particles from 0.1% to 50% by weight relative to the total weight of the dispersion, for example, from 10% to 30% by weight.

The spectral characteristics of these fluorescent particles can be varied by incorporating different TPE dyes. The fluorescent intensity of these polymer particles can be adjusted by varying the load concentration of the TPE dyes. The maximum TPE dye content in the polymer particles depends on the nature of the fluorochromes, the encapsulation technique used, the nature of the polymer constituting the particles and the size of these particles. Load concentration can depend on the functionalization density (the number of functional groups per particle) and the interaction (covalent or noncovalent) between the dye and the particles. The functionalization density depends on the size of the particles and the nature of the polymer (the polymer chain bearing functional groups), while the interaction depends on the nature of the fluorophores, the nature of the polymer, and the encapsulation technique used. The nature of the fluorophores depends on the kinds of functional groups they are facilitated. The maximum TPE dye content in the polymer particles may thus vary considerably and reach values of several million fluorochrome molecules per latex particle. The dye content of the presently described fluorescent polymer particles can be much higher in comparison to the conventional particles, owing to the absence of self-quenching of the TPE dyes. On the contrary, the fluorescence of the TPE dyes in this invention can be remarkably enhanced at high concentrations, resulting from the AIE effect of TPE dyes.

By using the processes of this invention, fluorescent polymer particles can be optimized in terms of size, polymer composition, surface chemistry, and/or spectral characteristics. The fluorescent polymer particles according to this invention may be used in all the conventional applications of polymer particles which are well known to those skilled in the art (paint, coating, cosmetic, marker, fluidic tracer, etc.). The fluorescent polymer particles according to the invention are more particularly intended for direct or indirect involvement in biological analyses.

EXAMPLES

The following examples are illustrative of the presently described subject matter and are not intended to be limitations thereon.

Example 1

1,2-Bis(4-hydroxyphenyl)-1,2-diphenylethylene (TPE-OH)

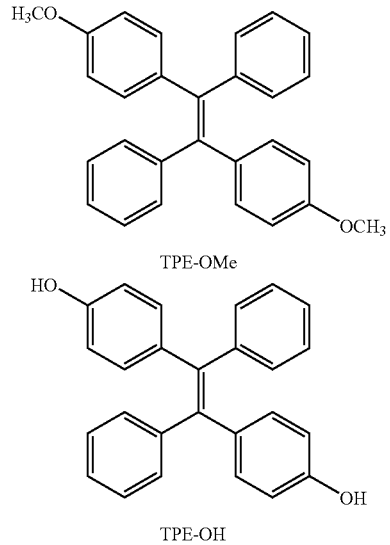

A suspension of p-methoxybenzophenone (1.06 g, 5.0 mmol), 1.34 equiv of $TiCl_3/AlCl_3$ (5.81 g, 6.7 mmol), and 25 equiv of Zn dust (8.01 g, 122.0 mmol) in 100 ml of dry THF was refluxed for 20 h. The reaction mixture was cooled to room temperature and filtered. The filtrates were evaporated and the crude product was purified by a silica gel column using hexane as eluent. 1,2-Bis(4-methoxyphenyl)-1,2-diphenylethene (TPE-OMe) was isolated in 91% yield.

TPE-OMe (1.40 g, 3.56 mmol) was dissolved in 20 ml of dichloromethane (DCM) in a 100 ml flask, and the flask was placed in an acetone-dry ice bath at −78° C. A solution of 3.59 g (14.3 mmol) of boron tribromide in 10 ml of DCM was added carefully to the mixture under stirring. The resultant mixture was allowed to warm to room temperature overnight under stirring. The reaction product was hydrolyzed by careful shaking with 20 ml of water. The organic phase was separated and concentrated by a rotary evaporator. The crude product was purified by recrystallization from THF/methanol to afford a white solid in 97% yield.

Characterization data of TPE-OMe: $^1H$ NMR ($CDCl_3$, 300 MHz) δ (ppm): 7.10-7.06 (m, 10H), 6.93 (t, 4H), 6.64 (t, 4H), 3.74 (s, 6H). $^{13}C$ NMR ($CDCl_3$, 75 MHz) δ (ppm): 158.0, 144.4, 139.7, 136.5, 132.6, 131.5, 127.8, 126.3, 113.2, 55.2. MS (TOF) m/e: 392.1 (M+, calcd. 392.2).

TPE-OH: $^1H$ NMR ($CDCl_3$, 300 MHz) δ (ppm): 7.11-7.02 (m, 10H), 6.88 (t, 4H), 6.56 (d, 4H). $^{13}C$ NMR ($CDCl_3$, 75 MHz) δ (ppm): 154.1, 144.2, 139.7, 135.5, 132.8, 131.5, 127.8, 126.3, 114.7. MS (TOF) m/e: 363.1 [(M-H)+, calcd: 363.1].

Example 2

1,2-Diphenyl-1,2-bis(4,4'-(3-sulfonato)propoxyl)phenylethylene (TPE-SO3)

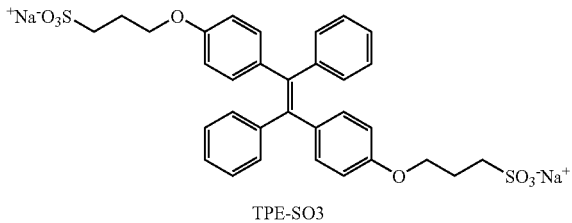

TPE-SO3

Into a 100 m round-bottom flask were added TPE-OH (0.5 g, 1.37 mmol) and 20 m of anhydrous ethanol under nitrogen. The mixture was stirred until all solids disappeared. A mixture of NaOEt (0.20 g, 3.0 mmol) in 20 ml ethanol was added dropwise and stirred for 1 h, causing the colorless solution to turn orange-red. Into the solution was added 0.35 g of 1,3-propanesultone (2.88 mmol) in 20 m of ethanol. The mixture was vigorously stirred for 12 h and a white product precipitated out from the solution. The product was collected by filtration and washed with ethanol and acetone twice to give a white solid in 61% yield.

Characterization data of TPE-SO3: $^1$H NMR (DMSO-d6, 300 MHz) δ (ppm): 7.25-7.13 (m, 6H), 7.08-7.02 (m, 4H), 6.95-6.90 (m, 4H), 6.81-6.73 (m, 4H), 4.09-4.02 (m, 4H), 2.66-2.58 (m, 4H), 2.08-2.02 (m, 4H). $^{13}$C NMR (DMSO-d6, 75 MHz) δ (ppm): 157.0, 143.9, 139.2, 135.5, 131.9, 130.8, 127.8, 126.2, 113.8, 66.4, 47.9, 25.3. MS (TOF) m/e: 631.1 [(M+2H)+–Na, calcd. 631.1], 609.2 [(M+3H)$^+$–2Na, calcd. 609.1].

Example 3

N,N'-[1,2-Diphenyl-1,2-bis(1,4-phenoxyethyl)vinyl]bis(triethylammonium bromide) (TPE-C2N+)

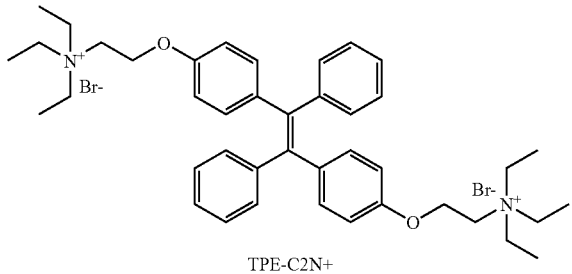

TPE-C2N+

To a mixture of sodium hydride (84 mg) and 1,2-bis(4-hydroxyphenyl)-1,2-diphenylethene (0.50 g) in dry dioxane (20 ml), 1,2-dibromoethane (1.50 g) was added at room temperature. The mixture was heated to reflux and stirred for 24 h. After filtration and concentration, the product was isolated and purified by silica gel chromatography using chloroform/hexane (1:1 v/v) as elute. 1,2-Bis[4-(2-bromoethoxy)phenyl]-1,2-diphenylethene (TPE-C2Br) was obtained in 32% yield.

A 250 ml flask with a magnetic spin bar was charged with TPE-C2Br (100 mg) dissolved in 100 ml of THF. To this solution was added triethylamine (5 ml). The mixture was heated to reflux and stirred for 3 days. During this period, 10 ml of water was added at several intervals. THF and extra triethylamine were evaporated. The water solution was washed by chloroform three times. After solvent evaporation, the residue was washed with chloroform and acetone and then dried overnight in vacuo at 50° C. TPE-C2N+ was isolated in 56% yield.

Characterization data of TPE-C2Br: $^1$H NMR (300 MHz, CDCl$_3$), δ (ppm): 7.10-7.02 (m, 10H), 6.95-6.92 (m, 4H), 6.65-6.59 (m, 4H), 4.15-4.11 (m, 4H), 3.55-3.49 (m, 4H). $^{13}$C NMR (75 MHz, CDCl$_3$), δ (ppm): 156.6, 144.1, 139.8, 137.2, 132.7, 131.5, 127.8, 126.4, 114.0, 67.8, 29.3. MS (TOF), m/e: 578.03 ([M]+, calcd. 578.03).

TPE-C2N+: $^1$H NMR (300 MHz, CDCl$_3$), δ (ppm): 7.09-7.00 (m, 10H), 6.97-6.87 (m, 4H), 6.61-6.54 (m, 4H), 3.90-3.84 (m, 4H), 3.45-3.40 (m, 4H), 2.00-1.97 (m, 4H), 1.88-1.84 (m, 4H). $^{13}$C NMR (75 MHz, CDCl$_3$), δ (ppm): 157.9, 144.9, 140.3, 137.2, 133.2, 132.1, 128.3, 126.9, 114.2, 67.3, 34.2, 30.2, 28.6. MS (TOF), m/e: 634.09 ([M]+, calcd. 634.09).

Example 4

N,N'-[1,2-Diphenyl-1,2-bis(1,4-phenoxybutyl)vinyl]bis(triethylammonium bromide) (TPE-C4N+)

The synthesis of the below compound was carried out according to Example 3 by using the corresponding dibromobutane.

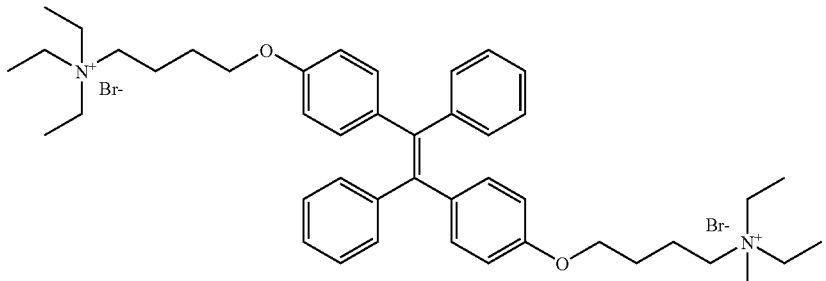

TPE-C4N+

Characterization data of TPE-C4Br: $^1$H NMR (300 MHz, CDCl$_3$), δ (ppm): 7.09-7.00 (m, 10H), 6.97-6.87 (m, 4H), 6.61-6.54 (m, 4H), 3.90-3.84 (m, 4H), 3.45-3.40 (m, 4H), 2.00-1.97 (m, 4H), 1.88-1.84 (m, 4H). $^{13}$C NMR (75 MHz, CDCl$_3$), δ (ppm): 157.9, 144.9, 140.3, 137.2, 133.2, 132.1, 128.3, 126.9, 114.2, 67.3, 34.2, 30.2, 28.6. MS (TOF), m/e: 634.09 ([M]+, calcd. 634.09).

TPE-C4N+: $^1$H NMR (300 MHz, d-DMSO), δ (ppm): 7.25-7.19 (m, 6H), 7.07-6.92 (m, 8H), 6.83-6.77 (m, 4H), 4.04-4.02 (m, 4H), 3.36-3.29 (m, 16H), 1.86-1.81 (m, 8H), 1.34-1.11 (m, 18H). $^{13}$C NMR (75 MHz, d-DMSO), δ (ppm): 156.9, 143.8, 139.3, 135.7, 132.0, 130.7, 127.9, 126.4, 113.7, 66.5, 55.6, 52.0, 25.5, 18.0, 7.2. MS (TOF), m/e: 789.50 ([M.2H$_2$O—HBr]+, calcd. 789.44).

Example 5

1,1,2,2-tetrakis(4-hydroxyphenyl)ethylene (DHTPE)

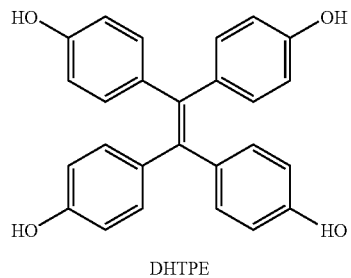

DHTPE

A suspension of 4,4'-dihydroxybenzophenone (3.0 g, 14.0 mmol), 1 equiv of TiCl$_4$ (1.54 ml, 14.0 mmol), and 2 equiv of Zn dust (1.83 g, 28.0 mmol) in 100 ml of dry THF was refluxed for 20 h. The reaction mixture was cooled to room temperature and filtered. The filtrates were evaporated and the crude product was purified by a silica gel column using ethyl acetate (EA) as eluent. DHTPE was obtained as slight yellow powder of 83% yield.

Characterization data of DHTPE: $^1$H NMR (300 MHz, d-DMSO), δ (ppm): 9.24-8.94 (br), 7.07-7.04 (d, 4H), 6.95-6.95 (d, 4H), 6.70-6.56 (m, 4H), 6.47-6.42 (t, 4H). $^{13}$C NMR (75 MHz, CDCl3), δ (ppm): MS (FAB), m/e: 391.2 ([M-4H]+, calcd. 392.1).

Example 6

N,N',N'',N'''-[1,2-Tetrakis(1,4-phenoxybutyl)vinyl] tetrakis(triethylammonium bromide) (N+C4-TPE-C4N+)

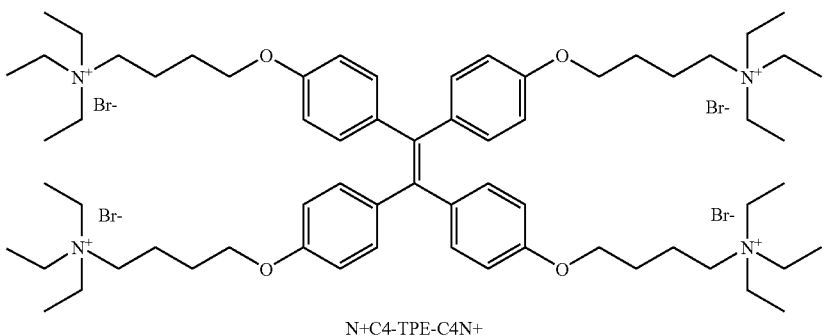

N+C4-TPE-C4N+

To a mixture of DHTPE (0.4 g, 20 mmol) and potassium carbonate in acetone, 1,4-dibromobutane (3 ml) was added and the mixture was heated to reflux and stirred for 24 h. After filtration and concentration, the product was isolated and purified by silica gel chromatography using chloroform/hexane (1:1 v/v) as eluent. The product 1,1,2,2-tetrakis(4-(4-bromobutoxy)phenyl)ethane (BrC4-TPE-C4Br) was obtained as white powder in 21% yield.

Characterization data of BrC4-TPE-C4Br: $^1$H NMR (300 MHz, CDCl$_3$), δ (ppm): 7.08-6.99 (m, 8H), 6.81-6.60 (m, 8H), 3.94-6.86 (m, 8H), 3.49-3.42 (m, 8H), 2.07-2.00 (m, 8H), 1.92-1.85 (m, 8H). $^{13}$C NMR (75 MHz, CDCl$_3$), δ (ppm): 157.2, 136.6, 132.7, 129.5, 114.3, 66.9, 33.9, 29.9, 28.3. MS (FAB), m/e: 937.0 ([M]+, calcd. 936.4).

N+C4-TPE-C4N+: $^1$H NMR (300 MHz, d-DMSO), δ (ppm): 7.29-7.27 (d, 1H), 7.10-7.08 (d, 1H), 6.83-6.80 (d, 7H), 6.83-6.80 (m, 7H), 3.91-3.83 (m, 8H), 3.23-3.18 (m, 16H), 2.89-2.84 (m, 8H), 1.70-1.65 (m, 20H), 1.17-1.06 (m, 40H). $^{13}$C NMR (75 MHz, d-DMSO), δ (ppm): 157.3, 135.6, 132.6, 130.6, 114.4, 67.2, 56.5, 52.9, 46.5, 26.4, 18.9, 8.0. MS (TOF), m/e: 933.6 ([M-4Br-3CH$_2$CH$_3$]+, calcd. 933.7).

Example 7

N,N',N'',N'''-[1,2-Tetrakis(1,4-phenoxyethyl)vinyl] tetrakis(triethylammonium bromide) (N+C2-TPE-C2N+)

The synthesis of the below compound was carried out according to Example 6 by using the corresponding dibromoethane.

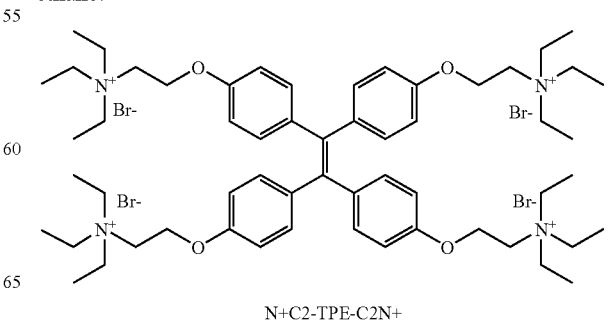

N+C2-TPE-C2N+

Characterization data of BrC2-TPE-C2Br: ¹H NMR (300 MHz, CDCl₃), δ (ppm): 7.71-7.70 (m, 1H), 7.54-7.53 (m, 1H), 7.10-7.07 (d, 4H), 6.93-6.90 (d, 3H), 6.84-6.82 (d, 4H), 6.65-6.63 (d, 3H), 4.28-4.22 (m, 8H), 3.63-3.60 (m, 8H). ¹³C NMR (75 MHz, CDCl3), δ (ppm): 156.7, 132.8, 130.0, 115.0, 114.1, 68.0, 29.6. MS (TOF), m/e: 823.9 ([M]+, calcd. 824.2).

N+C2-TPE-C2N+: ¹H NMR (400 MHz, D₂O), δ (ppm): 6.94-6.89 (m, 8H), 6.67-6.65 (m, 4H), 4.24-4.23 (m, 8H), 3.54-3.45 (m, 8H), 3.30-3.25 (m, 16H), 3.10-3.05 (m, 8H), 1.20-1.13 (m, 36H). ¹³C NMR (100 MHz, D₂O), δ (ppm): 156.2, 138.2, 133.1, 114.5, 98.0, 61.9, 56.0, 54.2, 54.1, 47.4, 9.1, 7.6. MS (FAB), m/e: 1222.5 ([M-2H]+, calcd. 1224.4).

Example 8

4,4'-(1,2-diphenylvinyl)di(phenylboronic acid) (TPE-BA)

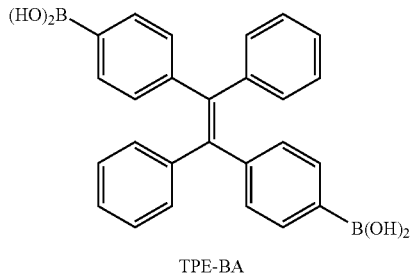

TPE-BA 1,2-bis(4-bromophenyl)-1,2-diphenylethene (0.4 g, 0.82 mmol) was dissolved in 20 ml of distilled tetrahydrofuran (THF) in a 100 ml flask, and the flask was placed in an acetone-dry ice bath at −78° C. A solution of 1.0 ml (2.6 mmol) of n-butyllithium (2.5 M in hexane) was added carefully to the mixture under stirring. After 1 h, 0.46 ml (4.0 mmol) of trimethyl borate was added to the solution and allowed to react for 45 min. The mixture was warmed to room temperature and overnight. Then dilute HCl was used to quench the reaction. After filtration and drying, the product was purified by silica gel column with ethyl acetate as eluent. The product was obtained as yellow solid in 54% yield.

Characterization data of TPE-BA: ¹H NMR (d-MeOH, 300 MHz) δ(ppm): 7.26-7.17 (m, 10H), 7.01-6.94 (m, 4H), 6.73-6.65 (m, 4H); ¹³C NMR (d-MeOH, 75 MHz), δ(TMS, ppm): 157.2, 146.2, 141.4, 137.0, 133.9, 132.7, 128.9, 127.4, 115.7; MS (TOF) m/e: 422.2 ([M-2H]+calcd: 420.1).

Example 9

4,4'-(1,2-diphenylvinyl)di(phenylcarboxylic acid) (TPE-CA)

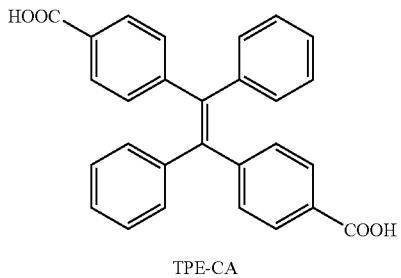

TPE-CA 1,2-bis(4-bromophenyl)-1,2-diphenylethene (1 g, 2.04 mmol) was dissolved in 20 ml of distilled tetrahydrofuran (THF) in a 100 ml flask, and the flask was placed in an acetone-dry ice bath at −78° C. A solution of 0.56 ml (6.12 mmol) of n-butyllithium (2.5 M in hexane) was added carefully to the mixture under stirring. The solution was transferred to a 500 ml flask with dry ice in it. The resultant mixture was stirred overnight under nitrogen at room temperature. After evaporation of THF, potassium hydroxide solution was added and the aqueous solution was washed by diethyl ether for several times. 3 M hydrochloric acid was used to acidify the aqueous solution. Ethyl acetate was used to extract the product. And the organic layer was dried with MgSO₄ to give the product with the yield of 24%.

Characterization data of TPE-CA: ¹H NMR (d-Acetone, 300 MHz) δ(ppm): 7.99-7.93 (m, 3H), 7.50-7.46 (m, 1H), 7.35-7.28 (m, 9H), 7.25-7.16 (m, 4H), 7.15-7.10 (m, 1H); ¹³C NMR (d-Acetone, 75 MHz), δ(TMS, ppm): 166.1, 147.8, 142.4, 142.3, 141.1, 132.6, 130.7, 130.5, 128.8, 128.4, 127.6, 127.3, 126.7, 126.3, 120.0; MS (TOF) m/e: 403.14 ([M-OH]+ calcd: 403.14).

Example 10

1,2-di[4-(aminomethyl)phenyl]-1,2-diphenylethylene (TPE-MA)

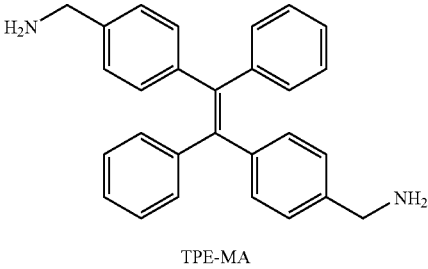

TPE-MA

A mixture of 1,2-diphenyl-1,2-dip-tolylethene (TPE-Me, 2 g, 5.6 mmol), NBS (2 g, 11.1 mmol) and a catalyst amount of benzoyl peroxide in carbon tetrachloride (50 ml) was gently refluxed for 8 h in a 150 ml round-bottom flask. After filtration and concentration, the product was isolated and purified by silica gel chromatography using chloroform/hexane (1:4 v/v) as eluent. 1,2-bis(4-(bromomethyl)phenyl)-1,2-diphenylethene (TPE-MB) was obtained as light yellow powder in 45% yield.

A mixture of TPE-MB (0.8 g, 1.5 mmol) and NaN₃ (0.1 g, 1.5 mmol) in DMSO (30 ml) was stirred under N₂ at room temperature for 18 h. The reaction mixture was added to water (200 ml) slowly, and then extracted with dichloromethane. The combined organic layers were dried with MgSO₄ and evaporated to dryness. The crude product was purified by silica gel chromatography eluting with 1:1 chloroform/hexane to give 1,2-bis(4-(azidomethyl)phenyl)-1,2-diphenylethene (TPE-MN3) as a white-off solid in 73% yield.

The azido-substituted TPE (TPE-MN3) (0.3 g, 0.7 mmol) was dissolved in dry THF (60 ml) and LiAlH₄ (0.15 g, 4.1 mmol) was added slowly at room temperature with constant stirring under nitrogen. Following the addition, the mixture was heated at reflux for 8 h. Water (5 ml-10 ml) was added slowly to decompose the excess LiAlH₄. The solution was then filtered and THF was used to wash the solid residue. After evaporation of the organic filtrate, dilute hydrochloric acid was added and the aqueous solution was washed by diethyl ether for several times. Ammonium hydroxide was used to basify the aqueous solution, following the extraction by diethyl ether. The organic layer was dried with Na₂SO₄ and evaporated to dryness. TPE-MA was obtained as light yellow powder in 87% yield.

Characterization data of TPE-MB: $^1$H NMR (CDCl$_3$, 300 MHz) δ(ppm): 7.14-7.07 (m, 10H), 7.02-6.96 (m, 8H), 4.42-4.40 (d, 4H); $^{13}$C NMR (CDCl$_3$, 75 MHz), δ(TMS, ppm): 144.4, 143.9, 141.5, 126.6, 132.3, 132.0, 129.2, 128.5, 127.4, 34.3; MS (TOF) m/e: 518.0 ([M]+ calcd: 518.2).

TPE-MN3: $^1$H NMR (CDCl$_3$, 300 MHz) δ(ppm): 7.12-7.07 (m, 6H), 7.04-6.99 (m, 12H), 4.24 (s, 4H); $^{13}$C NMR (CDCl$_3$, 75 MHz), δ(TMS, ppm): 144.4, 143.9, 141.5, 134.1, 132.4, 131.9, 128.5, 128.4, 127.3, 55.2; MS (TOF) m/e: 400.15 ([M-3N]+ calcd: 400.14)

TPE-MA: $^1$H NMR (d-MeOH, 300 MHz) δ(ppm): 7.10-7.06 (m, 10H), 7.00-6.93 (m, 8H), 3.75-3.70 (br, 4H); $^{13}$C NMR (CDCl$_3$, 75 MHz), δ(TMS, ppm): 143.9, 142.4, 140.7, 131.6, 131.4, 127.8, 127.7, 126.5, 126.4, 30.4; MS (TOF) m/e: 374.1 ([M-NH$_2$]+ calcd: 374.2)

Example 11

1,1'-Bis-[4-(N,N'-diethylaminomethyl)phenyl]-2,3,4,5-tetraphenylsilole (A$_2$-HPS) and N,N'-[1,1'-bis(1,4-benzylene)-2,3,4,5-tetraphenylsilolyl)bis(triethylammonium bromide) (HPS-(C1N+)2

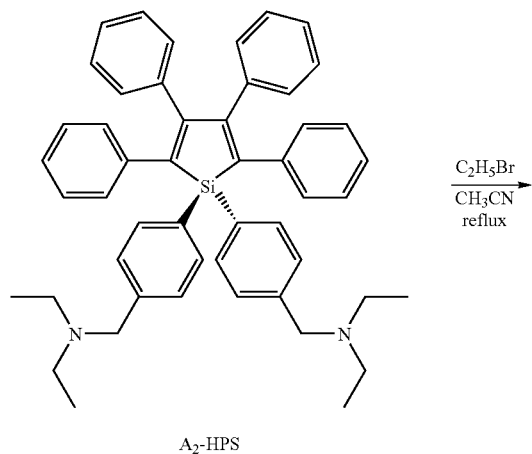

A$_2$-HPS

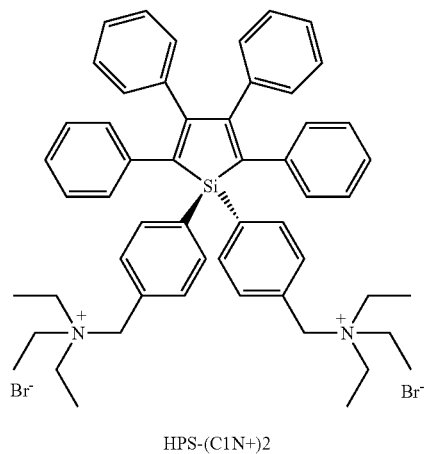

HPS-(C1N+)2

Into a 500 ml round-bottomed flask were added 150 ml THF, 5 ml water, 2.2 g potassium carbonate, 6 ml diethyl amine, and 5 g p-bromobenzyl bromide. The resultant mixture was refluxed for 12 h. The mixture was then cooled to room temperature, into which 6 ml concentrated HCl was added, followed by the addition of 150 ml water. The mixture was extracted with 100 ml diethyl ether for three times. The diethyl ether solution was dried with anhydrous magnesium sulfate over night and then the magnesium sulfate was removed by filtration. Diethyl ether was evaporated and the raw product was purified by a silica gel column using hexane/chloroform mixture (1:1 by volume) as the eluent. (p-bromobenzyl)diethyl amine (BBDA) was obtained in 74% yield (3.6 g).

Into a solution of tolan (5 g, 28 mmol) in THF (25 ml) was added under dry nitrogen lithium shaving (0.214 mg, 31 mmol). The mixture was stirred for 12 h at room temperature and the resultant green-blue colored THF solution was added dropwise to a solution of tetrachlorosilane (1.61 ml, 14 mmol) in 125 ml THF. The reaction mixture was stirred for 2 h at room temperature and then refluxed for 5 h.

Into another flask were added BBDA (6.8 g, 28 mmol) and 80 ml THF. The mixture was cooled to −78° C., into which 10 ml n-BuLi (2.5 M in hexane) was added. After stirring for 1.5 h, the mixture was transferred dropwise at −78° C. to the solution of chlorosilole (preparation shown in previous patent). The reaction mixture was allowed to warm to room temperature and was then stirred overnight at that temperature. Then THF was removed by evaporation, and the crude product was dissolved in diethyl ether. The solution was washed three times by water. The crude product was purified by a silica gel column using chloroform as the eluent at first and changed to ethyl acetate when no by product came out. The product A$_2$-HPS was obtained in 28% yield after recrystallization from actone/ethanol mixture.

Characterization data of BBDA: $^1$H NMR (CDCl$_3$, 300 MHz) δ(ppm): 7.40 (d, 2H), 7.23 (d, 2H), 3.51 (s, 2H), 2.50 (m, 4H), 1.04 (m, 6H).

A$_2$-HPS: $^1$H NMR (CDCl$_3$, 300 MHz) δ(ppm): 7.56 (d, 2H), 7.32 (d, 2H), 7.05-6.75 (m, br, 20H), 3.55 (s, 4H), 2.54 (m, 8H), 1.04 (m, 12H). $^{13}$C NMR (75 MHz, CDCl$_3$), δ (TMS, ppm): 156.6, 142.3, 140.0, 139.9, 139.0, 136.2, 130.2, 129.8, 129.0, 127.9, 127.6, 126.5, 125.7, 57.8, 47.2, 12.1. MS (CI): m/e calcd for C$_{50}$H$_{52}$N$_2$Si, 708.4, found 709.4 (M$^+$). UV (THF, 4.0×10$^{-5}$ mol/L), $\lambda_{max}$ (nm): 364. Melting point: 119-120° C. HPS-(C1N+)2 was obtained by refluxing A$_2$-HPS together with bromoethane in acetonitrile.

Example 12

Fluorimetric titration of biomacromolecules to polyenes
Bovine serum albumin (BSA) and calf thymus DNA (ctDNA) were selected as model proteins and DNA. BSA was dissolved in a pH 7.0 phosphate buffer solution (1.0 mg/ml). DNA was dissolved in deionized water (1.0 mg/ml) and filtered through a 0.45 μm filter. The actual concentration (in nucleic base) was determined by UV photometry using the extinction coefficient $\epsilon_{260}$=6600 M$^{-1}$ cm$^{-1}$.

Stock solutions of polyenes were 5×10$^{-4}$ M in water. Fluorescence titration was carried out by sequentially adding 100 μl aliquots of DNA or BSA solutions to a 100 μl stock solution of polyenes, followed by adding an aqueous phosphate buffer (10 mM, pH 7) to acquire a 10.00 ml solution. The mixtures were stirred for half an hour prior to taking their spectra. See FIGS. 1-10 and Table 1 below.

TABLE 1

Photophysical Properties of TPEs in Solution (soln),[a] Aggregate (aggr),[b] and Binding (bind)[c] States

| TPE | $\lambda_{ab}$, nm[d] | | $\lambda_{em}$, nm ($\Phi_F$, %)[e] | | |
|---|---|---|---|---|---|
| | soln | aggr | soln | aggr | bind |
| TPE-OMe | 311 | 330 | 394 (0.11) | 477 (15.30) | |
| TPE-OH | 312 | 316 | 393 (0.57) | 439 (8.90) | 467 (35.7) |
| TPE-SO3 | 312 | 320 | 398 (0.37) | 442 (17.47) | 472 (58.2) |

[a] In acetonitrile for TPE-OMe and TPE-OH (10 μM); in water for TPE-SO3 (5 μM).
[b] In 99% water/AN mixture for TPE-OMe and TPE-OH; in 99% AN/water mixture for TPE-SO3.
[c] In BSA solution of TPE-OH·Na$_2$ or TPE-SO3 in an aqueous phosphate buffer with pH = 7.0.
[d] Absorption maximum.
[e] Emission maximum (quantum yield given in the parentheses); excitation wavelength: 350 nm.

Example 13

Comparison of water soluble and non-water soluble tetraphenylethylene derivatives In this example, a group of AIE-active tetraphenylethylene (TPE) derivatives, i.e., derivatives 1-4 below, were synthesized and water-soluble cationic salts 3 and 4 were evaluated for their utility as bioprobes. In aqueous buffer solutions, these non-emissive fluorophores become highly emissive upon binding to protein and DNA molecules through noncovalent, such as hydrophobic and electrostatic, interactions.

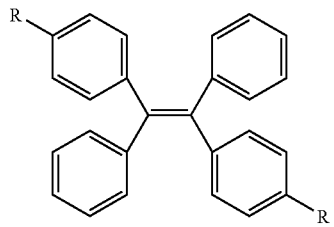

Derivative 1: R is —O(CH$_2$)$_2$Br
Derivative 2: R is —O(CH$_2$)$_4$Br
Derivative 3: R is —O(CH$_2$)$_2$N$^+$(C$_2$H$_5$)$_3$Br$^-$
Derivative 4: R is —O(CH$_2$)$_4$N$^+$(C$_2$H$_5$)$_3$Br$^-$ The TPE derivatives were prepared by the synthetic route as described herein. Reactions of 1,2-bis(4-hydroxyphenyl)-1,2-diphenylethene with α,ω-dibromoalkanes in the presence of sodium hydride yielded TPEs 1 and 2, whose quaternizations by NEt$_3$ gave salts 3 and 4, respectively. Molecular structures of the TPEs were characterized by spectroscopic techniques, from which satisfactory analysis data were obtained. Dyes 1 and 2 are soluble in common organic solvents such as acetonitrile (AN), chloroform and THF but insoluble in water. Salts 3 and 4, on the other hand, are soluble in water as well as in DMF and DMSO.

Figures 11A, 11B:
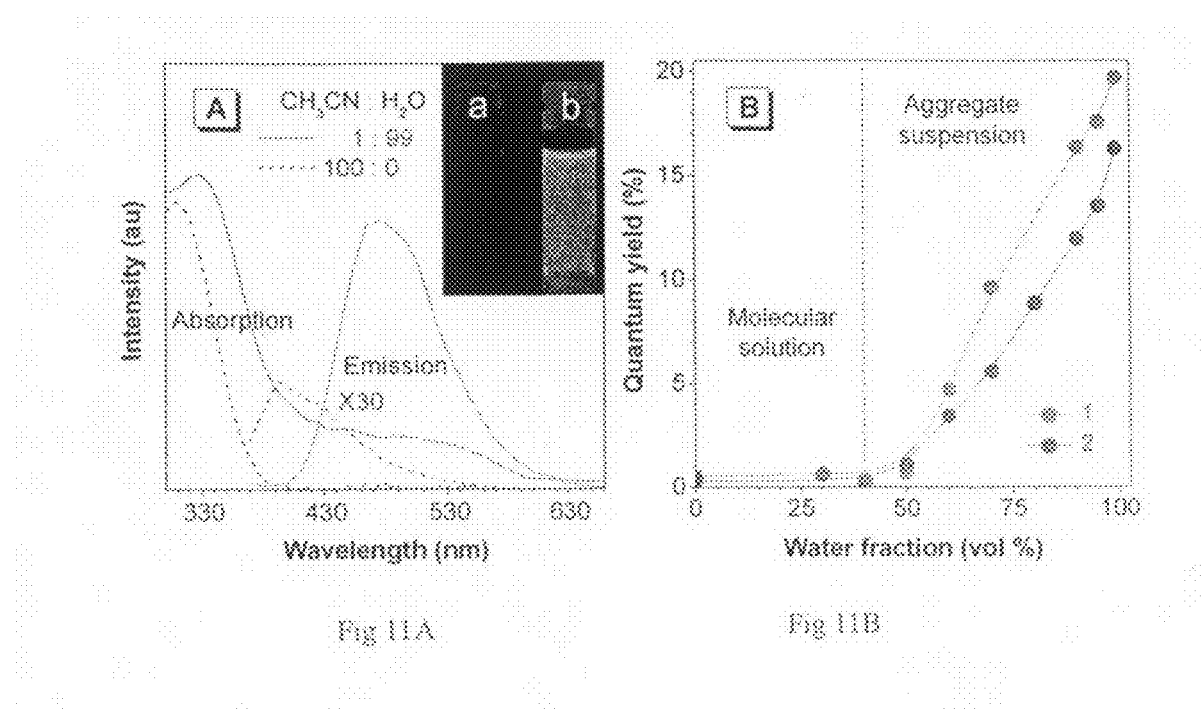
FIG. 11A illustrates the absorption and emission spectra of solutions of derivative 1 (10 µM) in AN and AN-water mixture (1:99 v/v). The inset is photographs of solutions of derivative 1 in (a) AN and (b) the AN-water mixture taken under illumination of a UV lamp.
FIG. 11B illustrates the dependence of fluorescence quantum yields of solutions of derivatives 1 and 2 on the solvent composition of AN-water mixture $\lambda_{ex}$=350 nm.

Dilute solutions of TPEs 1 and 2 in AN are practically non-luminescent. Addition of non-solvent water into the AN solutions can turn on the emissions of the dyes. From the molecular solution in AN to the aggregate suspension in an AN-water mixture (1:99 by volume), the fluorescent intensity of TPE 1 at 476 nm is increased by ~240 fold (FIG. 11A). Its absorption maximum shifts from 310 nm in the solution to 330 nm in the suspension. The excitation maximum of TPE 1 locates at 330 nm, coinciding well with its absorption maximum. The formation of nanoscopic aggregates of TPE 1 is suggested by the level-off tail in the visible region of its absorption spectrum due to the Mie effect of the nanoparticles. Evidently, the emission of TPE 1 is induced by the aggregate formation, or in other words, TPE 1 is AIE-active.

The change of $\emptyset_F$ value of TPE 1 with water fraction in the AN-water mixture further reveals its AIE characteristics (FIG. 11B). In the mixtures with water fractions below ~40%, TPE 1 exhibits negligibly small $\emptyset_F$ values (~0.5%) because the dye molecules are actually dissolved in the mixtures. The $\emptyset_F$ value of TPE 1 starts to increase when the water fraction is increased to ~50%, at which the solvating power of the mixture is decreased to such an extent that the dye molecules begin to aggregate. The $\emptyset_F$ value reaches ~20% at a water content of 99%, which is ~40-fold higher than that of its AN solution. The absolute $\emptyset_F$ values of the aggregates should be much higher than the relative $\emptyset_F$ values given in FIG. 11B, because the determination of the latter did not take into consideration the strong absorption caused by the Mie effect of the aggregates. TPE 2 exhibits similar AIE behavior. TPE Salts 3 and 4 are soluble in water. Addition of methanol, AN, THF and dioxane to their water solutions do not cause the salts to aggregate, possibly due to their amphiphilic nature. Their emissions in the mixtures remain as faint as those in the water solutions. However, increasing the concentrations of the salts can increase their $\emptyset F$ values, indicating that the salts are also AIE-active.

Complexation of the water-soluble AIE TPEs 3 and 4 with calf thymus DNA (ctDNA) and bovine serum albumin (BSA) were investigated by spectrometric titrations in aqueous phosphate buffer (pH=7.0) at 25° C. Stock solutions of TPEs 3 and 4 (0.25 mM) were prepared. The mixture of 100 μl stock solution of 3 with 9.9 ml buffer emits faintly at 395 nm with a side band at 462 nm. Its absorption maximum locates at 311 nm, with a molar absorptivity of 12400M$^-$1 cm$^-$1. Upon addition of the DNA, FL intensity of TPE 3 increased by 5.4 fold. Meanwhile its emission maximum shifted to ~462 nm, giving a Stokes shift as large as 134 nm. In the DNA concentration range of 0-100 μg/ml$^{-1}$, the plot of the FL intensity (I) at 462 nm as a function of DNA concentration (c) is a linear line with a correlation coefficient of 0.996. Addition of BSA to a buffer solution of TPE 3 induced a similar effect. The linear range of the I/I$_o$-1 vs. c plot in this case is 0-50 μg/ml$^{-1}$. The excitation maximums of the solutions of TPE 3 containing BSA and ctDNA both locate at 328 nm.

The effects of the biopolymers on the FL properties of TPE 4 are much more pronounced. As can be seen from FIG. 12, I/I$_o$ values as high as 16.3 and 23.8 are achieved when 300 μg/ml$^{-1}$ ct DNA and 500 μg/ml$^{-1}$ BSA are added into solutions of TPE 4, respectively. Clearly TPE 4 is a more sensitive bioprobe. The excitation maximum of TPE 4 is at 328 nm and the Stokes shift is ~135 nm. The linear ranges of TPE 4 are narrower: 0-20 μg/ml$^{-1}$ for DNA and 0-40 μg/ml$^{-1}$ for BSA. It is clear that the AIE salts TPEs 3 and 4 can be used as light-up bioprobes for DNA and protein detection. The probing sensitivity and linear range can be tuned by modifying their structures.

Regarding the origin of the emission induced by the addition of the biomacromolecules, the correlation with the AIE nature of the dyes must be considered. In both cases, similar shifts in the fluorescent maximums (from 390-399 nm to 463-478 nm) are observed. The excitation spectra of the biopolymer-induced emissions are also similar to those of the AIEs for the TPE derivatives. These facts lead to a natural conclusion that the strong blue emissions are from the same excited species.

It appears that the restriction of intramolecular rotations in the aggregates of AIE dyes may have blocked their nonradiative channels, thus making them highly emissive. If the AIE process of the TPE dyes follows the same mechanism, they should become emissive in the solutions with high viscosities at low temperatures, because under these conditions their intramolecular rotations would be hampered. The fluorescent behaviors of TPE 4 were thus investigated in a highly viscous glycerol-water (99:1 by volume) mixture at different temperatures. At 25° C., the glycerol-water solution of TPE 4 emits a strong blue light of 467 nm with a Stokes shift of 147 nm (FIG. 13), demonstrating that the high viscosity indeed helps. As the solution temperature is decreased from 25 to −5° C., the FL intensity of TPE 4 is increased as expected. Its excitation maximum locates at 328 nm, close to those of its nanoscopic aggregates and its complexes with the biopolymers.

It is well known that fast conformational exchanges caused by fast intramolecular rotations give sharp NMR resonance peaks, which can be broadened by cooling because the rotations and hence the exchanges become slower at lower temperatures. Dynamic NMR experiments of a dichloromethane solution of 1 reveals that its resonance peaks are broadened with a decrease in temperature. The plot of $\delta_{fwhm}$ vs. 1/T gives a linear line, indicating a single mechanism for the peak broadening. All these results confirm that the restriction of intramolecular rotations plays a crucial role in the AIE process. We now may envision how the emissions of the TPE salts are turned on by the addition of the biomacromolecules. In the buffer solutions containing the DNA and BSA, the cationic amphiphilic dyes bind to the biomacromolecules via noncovalent interactions, such as electrostatic attraction (especially for the negative-charged DNA) and hydrophobic effect (particularly for the protein with hydrophobic pockets in its native folding structure). When docked on the surfaces of the biopolymers and in the cavities of their folding structures, the dye molecules aggregate with the aid of strong electronic and hydrophobic interactions between their aryl rings. This suppresses intramolecular rotations of the dye molecules, which in turn impedes their radiationless transitions and activates their fluorescent processes. Thanks to the AIE nature, the emissions of the TPE-biopolymer complexes are greatly intensified with increasing concentration, for the TPE 4-BSA complex. This is truly remarkable, because conventional fluorescent probes suffer from the ACQ problem at high dye concentrations. In summary, in this example, we have successfully developed AIE active, water-soluble, conjugated polyene compounds (cationic dyes) for protein and DNA detection in aqueous media for the first time. The nonemissive dye solutions become emissive upon addition of the biomacromolecule, for example, DNA and/or BSA. These AIE compounds exhibit large molar absorptivities, high quantum yields and wide Stokes shifts and are thus ideal "turn-on" fluorescent bioprobes. The restriction of their intramolecular rotations plays a critical role in their AIE processes. Accordingly, any molecule whose electronic conjugation is affected by the twisting of multiple pendants around its core due to involved steric effects can be AIE active. This example demonstrates that AIE luminophors can be utilized as fluorescent probes in the area of biological research.

Example 14

Synthesis of 4,4'-(1,2-diphenylvinyl)di(phenylcarboxylic acid) (TPE-COOH)

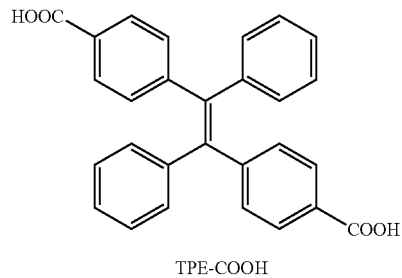

TPE-COOH

The scheme of the synthesis of TPE-COOH is shown in Scheme 1 above. 1,2-bis(4-bromophenyl)-1,2-diphenylethene (1 g, 2.04 mmol) was dissolved in 20 ml of distilled tetrahydrofuran (THF) in a 100 ml flask, and the flask was placed in an acetone/dry ice bath at −78° C. A solution of 0.56 ml (6.12 mmol) of n-butyllithium (2.5 M in hexane) was added carefully to the mixture under stirring. The solution was transferred to a 500 ml flask with dry ice in it. The resultant mixture was stirred overnight under nitrogen at room temperature. After evaporation of THF, potassium hydroxide solution was added and the aqueous solution was washed by diethyl ether for several times. 3 M hydrochloric acid was used to acidify the aqueous solution. Ethyl acetate was used to extract the product. And the organic layer was dried with $MgSO_4$ to give the product with the yield of 24%.

Characterization data of TPE-COOH: $^1H$ NMR (d-Acetone, 300 MHz) δ(ppm): 7.99-7.93 (m, 3H), 7.50-7.46 (m, 1H), 7.35-7.28 (m, 9H), 7.25-7.16 (m, 4H), 7.15-7.10 (m, 1H); $^{13}C$ NMR (d-Acetone, 75 MHz), δ(TMS, ppm): 166.1, 147.8, 142.4, 142.3, 141.1, 132.6, 130.7, 130.5, 128.8, 128.4, 127.6, 127.3, 126.7, 126.3, 120.0; MS (TOF) m/e: 403.14 ([M-OH]+ calcd: 403.14).

Figure 14:
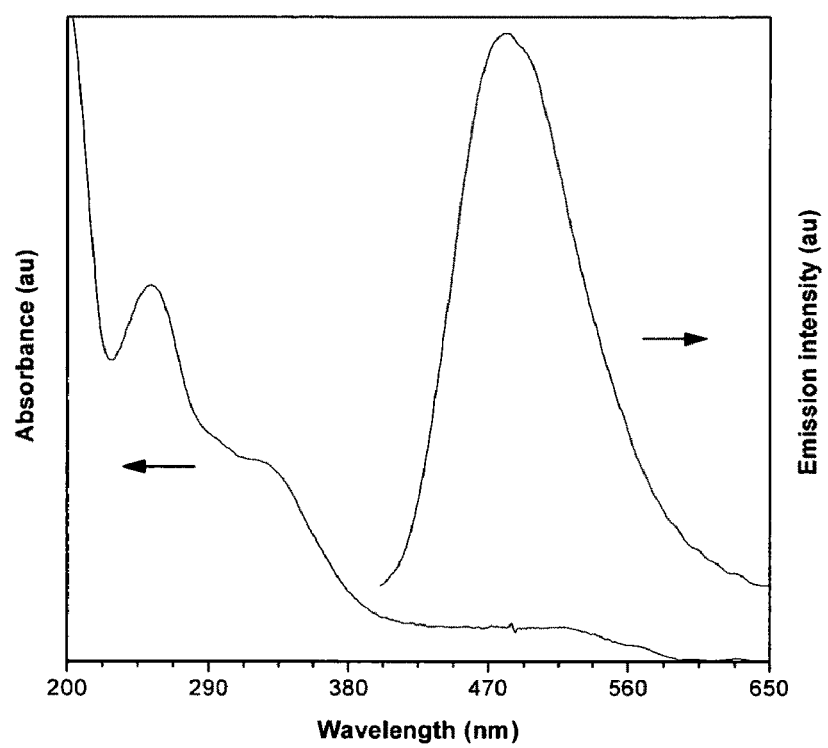
FIG. 14 illustrates the absorption and photoluminescence spectra of TPE-COOH in acetonitrile/water mixture (1:99 v/v). TPE-COOH concentration: 10 µM; excitation wavelength: 346 nm.

The absorption and photoluminescence spectra of the dye in acetonitrile/water mixture (1:99 v/v) are shown in FIG. 14. When it is molecularly dissolved in acetonitrile, it is practically nonfluorescent. However, when large amount of water (insoluble to TPE-COOH yet miscible with acetonitrile) is added, bright cyan light (~480 nm) is observed. The emission becomes stronger with an increase in water content, suggesting that TPE-COOH is AIE-active.

Example 15

Synthesis of 1,2-Bis(4-hydroxyphenyl)-1,2-diphenylethylene (TPE-OH)

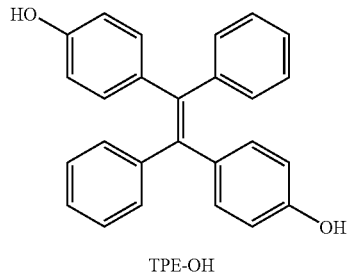

TPE-OH

A suspension of p-methoxybenzophenone (1.06 g, 5.0 mmol), 1.34 equiv of $TiCl_3/AlCl_3$ (5.81 g, 6.7 mmol), and 25 equiv of Zn dust (8.01 g, 122.0 mmol) in 100 ml of dry THF was refluxed for 20 h. The reaction mixture was cooled to room temperature and filtered. The filtrates were evaporated and the crude product was purified by a silica gel column using hexane as eluent. 1,2-Bis(4-methoxyphenyl)-1,2-diphenylethene (TPE-OMe) was isolated in 91% yield.

TPE-OMe (1.40 g, 3.56 mmol) was dissolved in 20 ml of dichloromethane (DCM) in a 100 ml flask, and the flask was placed in an acetone-dry ice bath at −78° C. A solution of 3.59 g (14.3 mmol) of boron tribromide in 10 ml of DCM was added carefully to the mixture under stirring. The resultant mixture was allowed to warm to room temperature overnight under stirring. The reaction product was hydrolyzed by careful shaking with 20 ml of water. The organic phase was separated and concentrated by a rotary evaporator. The crude product was purified by recrystallization from THF/methanol to afford a white solid in 97% yield.

Characterization data of TPE-OMe: $^1$H NMR ($CDCl_3$, 300 MHz) δ (ppm): 7.10-7.06 (m, 10H), 6.93 (t, 4H), 6.64 (t, 4H), 3.74 (s, 6H). $^{13}$C NMR ($CDCl_3$, 75 MHz) δ (ppm): 158.0, 144.4, 139.7, 136.5, 132.6, 131.5, 127.8, 126.3, 113.2, 55.2. MS (TOF) m/e: 392.1 (M+, calcd. 392.2).

Characterization data of TPE-OH: $^1$H NMR ($CDCl_3$, 300 MHz) δ (ppm): 7.11-7.02 (m, 10H), 6.88 (t, 4H), 6.56 (d, 4H). $^{13}$C NMR ($CDCl_3$, 75 MHz) δ (ppm): 154.1, 144.2, 139.7, 135.5, 132.8, 131.5, 127.8, 126.3, 114.7. MS (TOF) m/e: 363.1 [(M-H)+, calcd: 363.1].

Example 16

Preparation of Fluorescent Polymer Particles

Into a 50 ml dropping funnel was dissolved 0.1 wt % TPE-COOH in a monomer mixture of methyl methacrylate, butyl acrylate and 2-hydroxyethyl methacrylate, with the volume ratio of 4:5:1. The solution was purged with nitrogen for 20 min and then added dropwise into the deionized water containing the emulsifier sodium dodecyl sulfate (0.2 wt %). The emulsion copolymerization proceeds at 75° C. under 400 rpm agitation for 6-10 h then stops by cooling.

Figure 15:
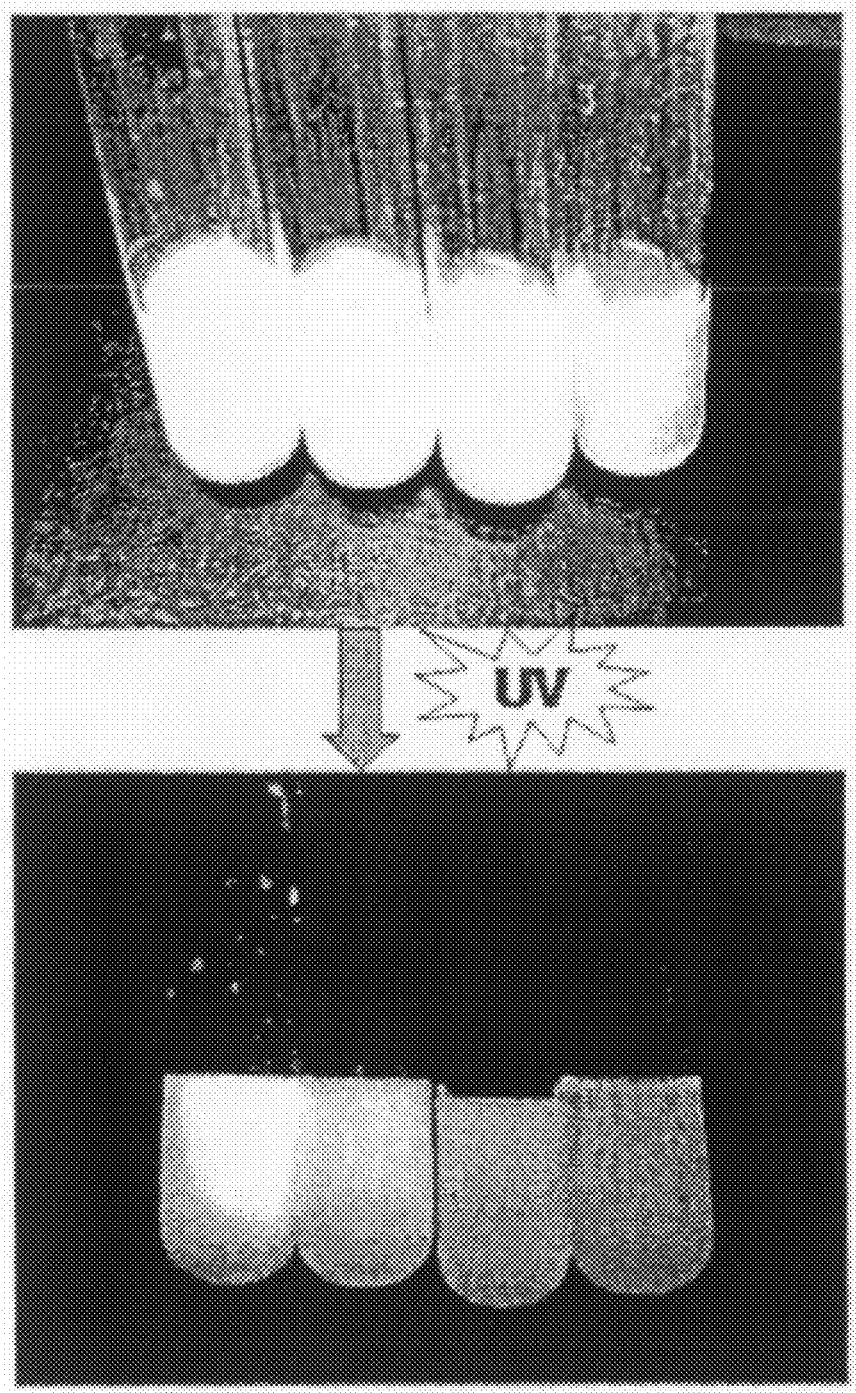
FIG. 15 illustrates the light emission of the fluorescent polymer particle dispersion of Example 16 with various dilutions: 100%, 20%, 5%, 1% (from left to right).

The polymer particle dispersion prepared is quite uniform and stable. The particle dispersion is highly emissive under UV irradiation, even in very dilute state (FIG. 15). It is worthy of noting that the emission of emulsion does not fade even when it is stored for several months under ambient temperature without any protection from light and air. This is due to the high stability of TPE molecules, which is distinctly different from other dye molecules that are prone to be bleached under room illumination.

Example 17

Preparation of Fluorescent Polymer Particles

The procedures are just the same as that in Example 16, except that the ratio of TPE-COOH decreases to 0.05 wt % relative to the monomer mixture of methyl methacrylate, butyl acrylate and 2-hydroxyethyl methacrylate (4:5:1 in volume).

Figure 16:
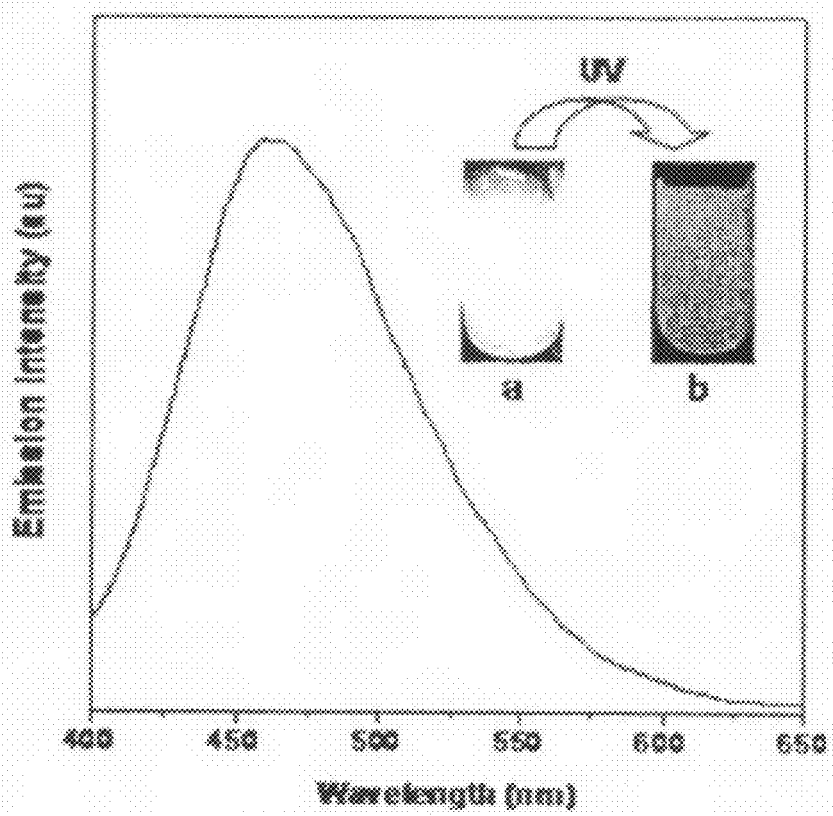
FIG. 16A illustrates the photoluminescence spectrum of the polymer particle dispersion of Example 17 containing TPE-COOH fluorophores. Concentration of the polymer in emulsion: 0.5 wt %; ratio of TPE-COOH to polymer: 0.1%; excitation wavelength: 346 nm.
FIG. 16B illustrates photographs of the polymer nanoparticle emulsion of Example 17 under normal room illumination (a) and 365 nm irradiation from a UV lamp (b).

The polymer particle dispersion prepared is quite uniform and stable. The particle dispersion is highly emissive under UV irradiation, even in very dilute state. The photoluminescence spectrum of the dispersion is shown in FIG. 16. The emission peak is found at 458 nm, which is somewhat blue shifted compared to the pure TPE-COOH.

Example 18

Preparation of Fluorescent Polymer Particles

The procedures are just the same as that in Example 17, except that the ratio of methyl methacrylate, butyl acrylate and 2-hydroxyethyl methacrylate changes to 5:4:1 in volume.

Figure 17:
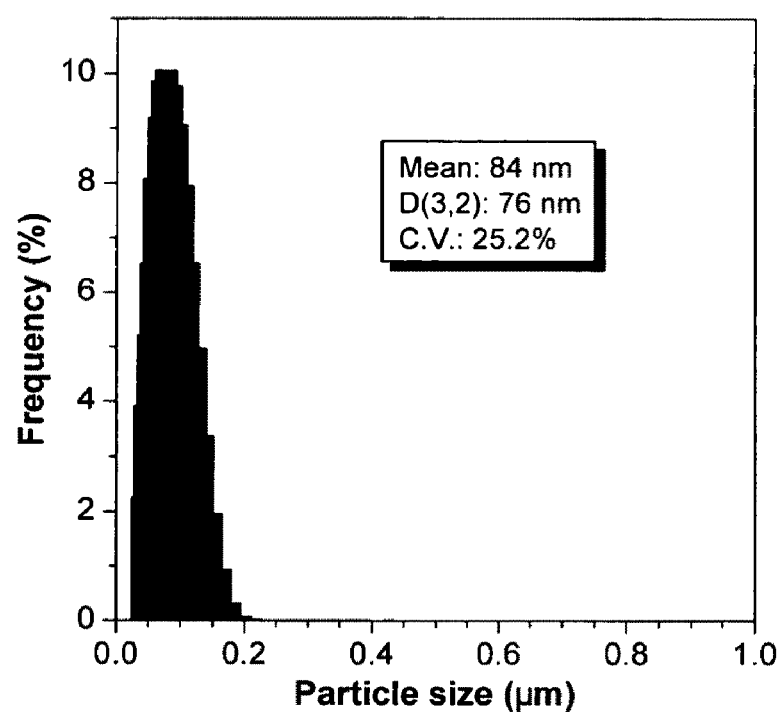
FIG. 17 illustrates the particle size and size distribution of the fluorescent polymer particles of Example 18. The inset shows the number-average diameter (Mean), weight-average diameter (D(3,2)), and coefficient of variation (C.V.) for the particles.

The polymer particle dispersion prepared is quite uniform and stable. The particle dispersion is highly emissive under UV irradiation, even in very dilute state. The particle size distribution of the polymer nanoparticles in the emulsion was shown in FIG. 17. The diameter of the polymer nanoparticles is on the average of ~80 nm, and the size distribution is narrow.

Example 19

Preparation of Fluorescent Polymer Particle

The procedures are just the same as that in Example 17, except that the emulsifier concentration decreases to 0, that is, the emulsion polymerization proceeds in the absence of emulsifier.

Figure 18A:
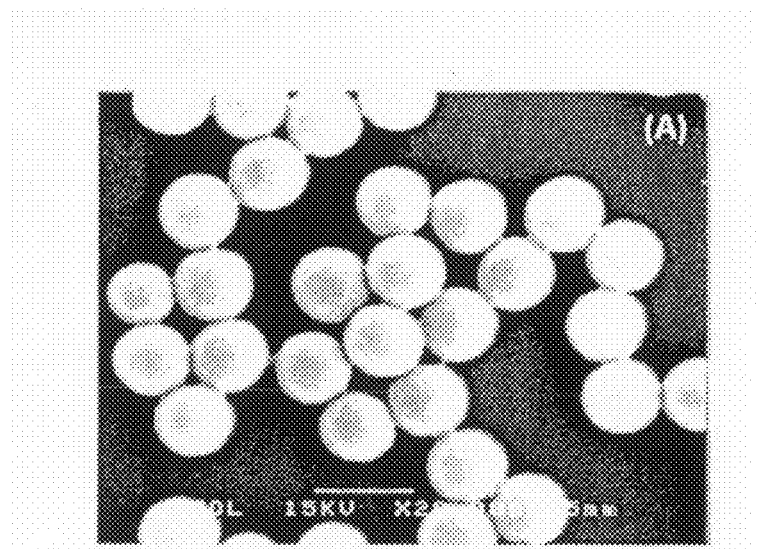
FIG. 18A is a scanning electron micrograph image of the fluorescent polymer particles of Example 19 prepared at a surfactant concentration of 0.

The polymer particle dispersion prepared is quite uniform. The particles tend to precipitate, however, they are readily be redispersed upon agitation. The particle dispersion is highly emissive under UV irradiation, even in very dilute state. The SEM image of the fluorescent polymer particles are shown in FIG. 18A, indicating a 760 nm particle size.

Example 20

Preparation of Fluorescent Polymer Particles

The procedures are just the same as that in Example 17, except that the emulsifier concentration decreases to 0.02 wt %.

Figure 18B:
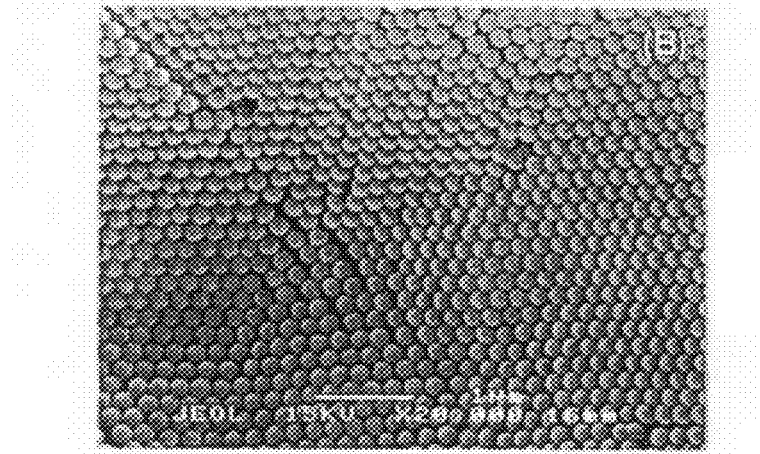
FIG. 18B is a scanning electron micrograph image of the fluorescent polymer particles of Example 20 prepared at a surfactant concentration of 0.02 wt %.

The polymer particle dispersion prepared is quite uniform and stable. The particle dispersion is highly emissive under UV irradiation, even in very dilute state. The SEM image of the fluorescent polymer particles are shown in FIG. 18B, indicating a 250 nm particle size.

Example 21

Preparation of Fluorescent Polymer Particles

The procedures are just the same as that in Example 17, except that the emulsifier concentration decreases to 0.04 wt %.

Figure 18C:
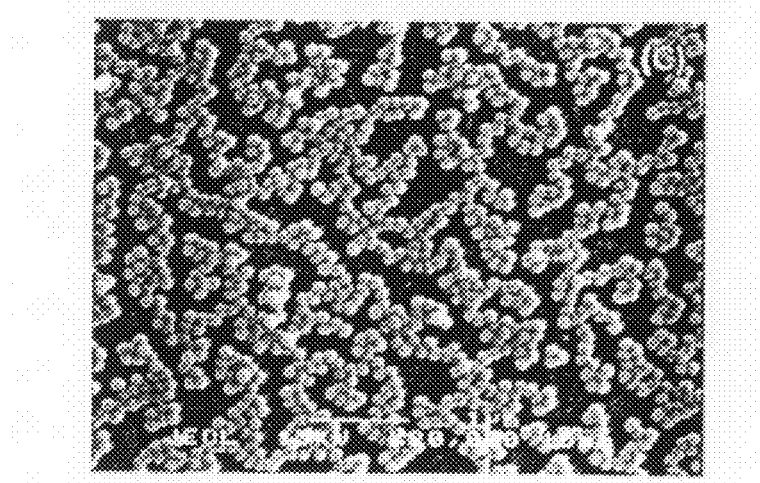
FIG. 18C is a scanning electron micrograph image of the fluorescent polymer particles of Example 21 prepared at a surfactant concentration of 0.04 wt %.

The polymer particle dispersion prepared is quite uniform and stable. The particle dispersion is highly emissive under UV irradiation, even in very dilute state. The SEM image of the fluorescent polymer particles are shown in FIG. 18C, indicating a 120 nm particle size.

Example 22

Preparation of Fluorescent Polymer Particles

The procedures are just the same as that in Example 17, except that 2-hydroxyethyl methacrylate is replace by acrylic acid.

The polymer particle dispersion prepared is quite uniform and stable. The particle dispersion is highly emissive under UV irradiation, even in very dilute state. The fluorescent particles have carboxyl functional groups on the surface, which is favorable to the bioconjugation.

Example 23

Preparation of Fluorescent Polymer Particles

The procedures are just the same as that in Example 18, except that 2-hydroxyethyl methacrylate is replace by acrylamide.

The polymer particle dispersion prepared is quite uniform and stable. The particle dispersion is highly emissive under UV irradiation, even in very dilute state. The fluorescent particles have amine functional groups on the surface, which is favorable to the bioconjugation.

Example 24

Preparation of Fluorescent Polymer Coating

Figure 19:
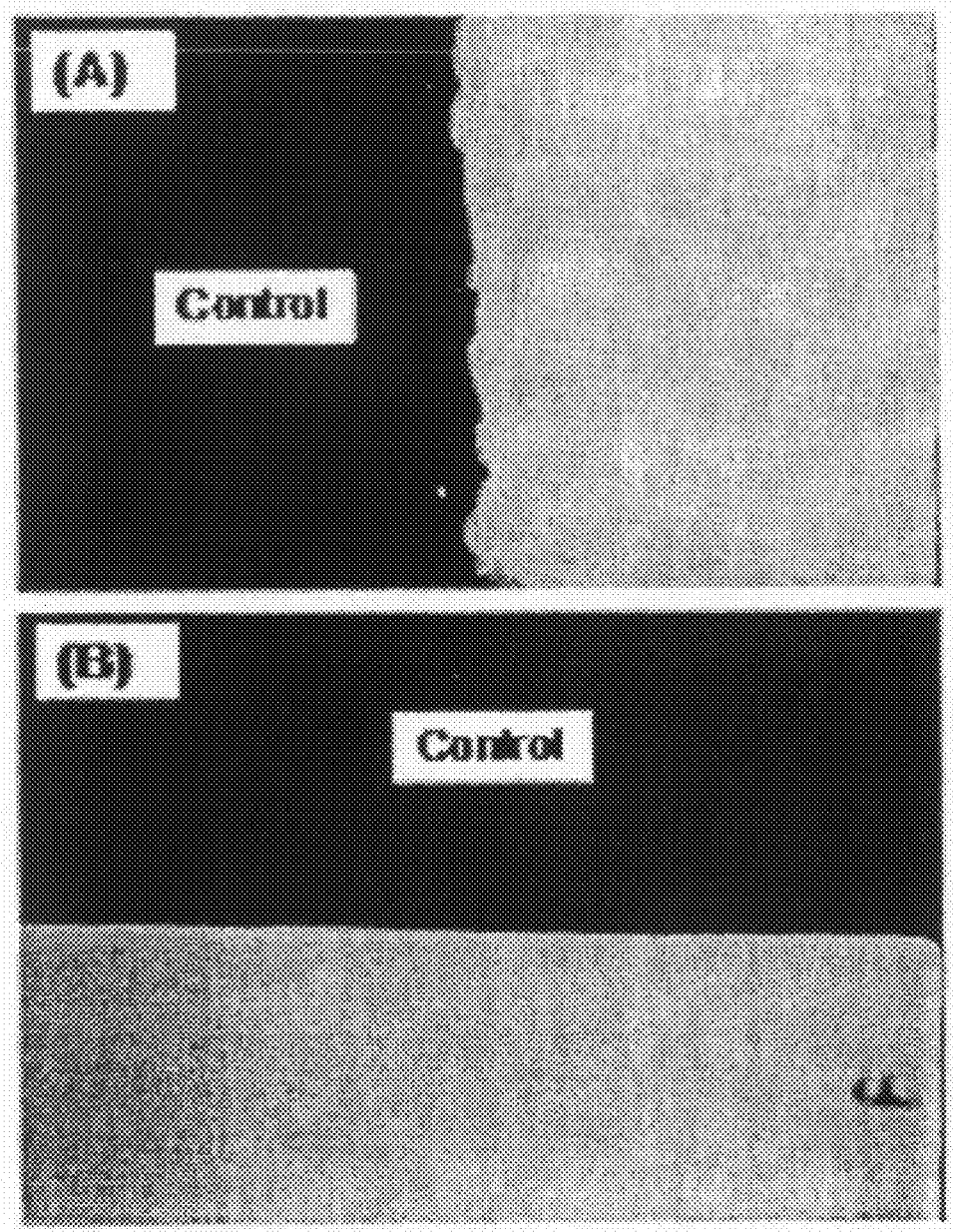
FIG. 19A is a photograph of the coating film of Example 24 formed by the polymer nanoparticle dispersion with and without (controls) TPE-COOH fluorophores. The photos were taken under 365 nm irradiation from a UV lamp.
FIG. 19B is a photograph of the flexible thin sheets of Example 25 formed by the polymer nanoparticle dispersion with and without (controls) TPE-COOH fluorophores. The photos were taken under 365 nm irradiation from a UV lamp.

The procedures for preparation of fluorescent dispersion are just the same as that in Example 17. The particle dispersion is highly emissive under UV irradiation, even in very dilute state. The size of the fluorescent particle is less than 100 nm and the glass transition temperature is below room temperature. The dispersion prepared in this invention is suitable for film formation, and the fluorescent coating film is shown in FIG. 19A. The coating film formed by control dispersion is nonluminescent while that formed by the fluorescent particle dispersion is highly emissive under UV irradiation.

Example 25

Preparation of Fluorescent, Free-Standing, Flexible Polymer Film

The procedures for preparation of fluorescent dispersion are just the same as that in Example 17. The particle dispersion is highly emissive under UV irradiation, even in very dilute state. The size of the fluorescent particle is less than 100 nm and the glass transition temperature is below room temperature. The dispersion prepared in this invention is suitable for film formation. With a PTFE mold, a free-standing flexible film can be facilely fabricated, and the fluorescent film is shown in FIG. 19B. The coating film formed by control dispersion is nonluminescent while that formed by the fluorescent particle dispersion is highly emissive under UV irradiation. Such fluorescent free-standing flexible polymer film can be used as flexible organic optoelectronic devices.

Example 26

The fluorescent polymer nanoparticles with amino groups were prepared with the method demonstrated in Example 23. The nanoparticle suspension was diluted 10 times by minimum essential media. Then 10 mg of transferrin (Tf) was added into this mixture and gently stirred at room temperature for 2 hours to allow the protein to covalently bond to the particle surface. The human cancer cell lines HeLa was cultured in Dulbecco minimum essential media with 10% fetal bovine serum (FBS), 1% penicillin, and 1% amphotericin B. The day before treatment, cells were seeded in 35 mm culture dishes at a confluency of 70-80%. On the treatment day, the cells in serum-supplemented media were treated with the Tf-conjugated nanoparticles for 2 hours at 37° C. Afterwards, the cells were washed three times with PBS and directly imaged using a fluorescent microscope.

Figure 20A:
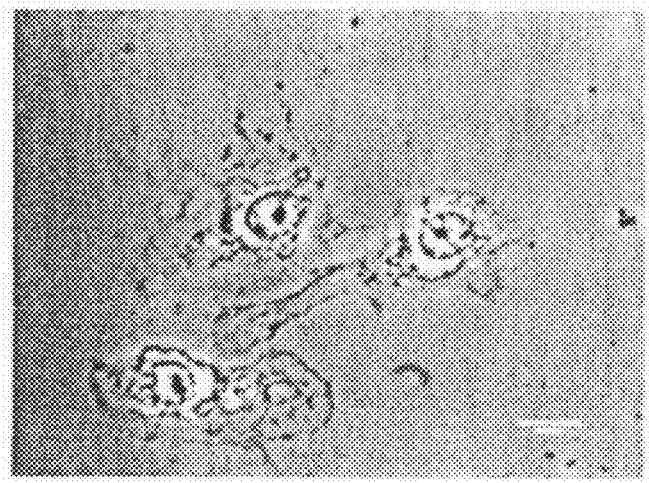
FIG. 20A is a transmission electron micrograph image of HeLa cell treated with the fluorescent polymer nanoparticles of Example 26.
Figure 20B:
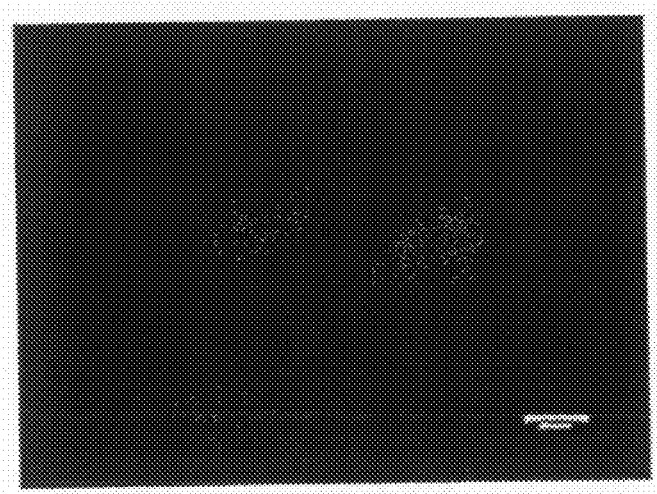
FIG. 20B is a transmission electron micrograph image of HeLa cells treated with the fluorescent polymer nanoparticles of Example 26 upon excitation of 365 nm UV light.

The results are shown in FIG. 20. From the microscopic fluorescence images, it can be seen that the whole cells are bright, indicating that the fluorescent nanoparticles have migrated into the cells. In other words, they are labeled.

Results on cell labeling using the fluorescent polymer nanoparticles have been obtained. As shown below, 48 nm fluorescent polymer nanoparticles were first prepared with amino groups on the surface, and then bioconjugation of transferring, a known protein that tends to target HeLa cells, was carried out. Subsequently, the HeLa cells in serum-supplemented media were treated with the particle-transferrin conjugates. As a result, transferring-conjugated nanoparticles were transported into the cells through the transferrin receptor mediated endocytosis pathway. Since transferrin receptors are minimally distributed in normal cells, transferrin serves as an excellent ligand for preferentially targeting cancerous cells in vitro and in vivo. From the microscopic fluorescence image (FIG. 20), it can be seen that the whole cells are bright, indicating that the fluorescent nanoparticles have migrated into the cells. In other words, they are labeled.

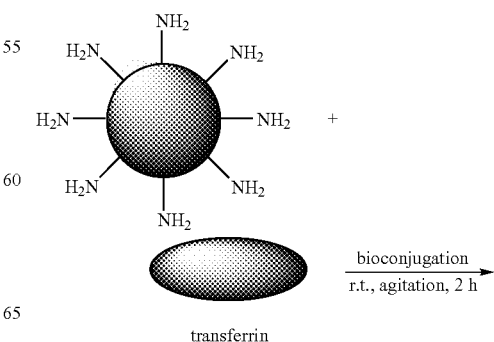

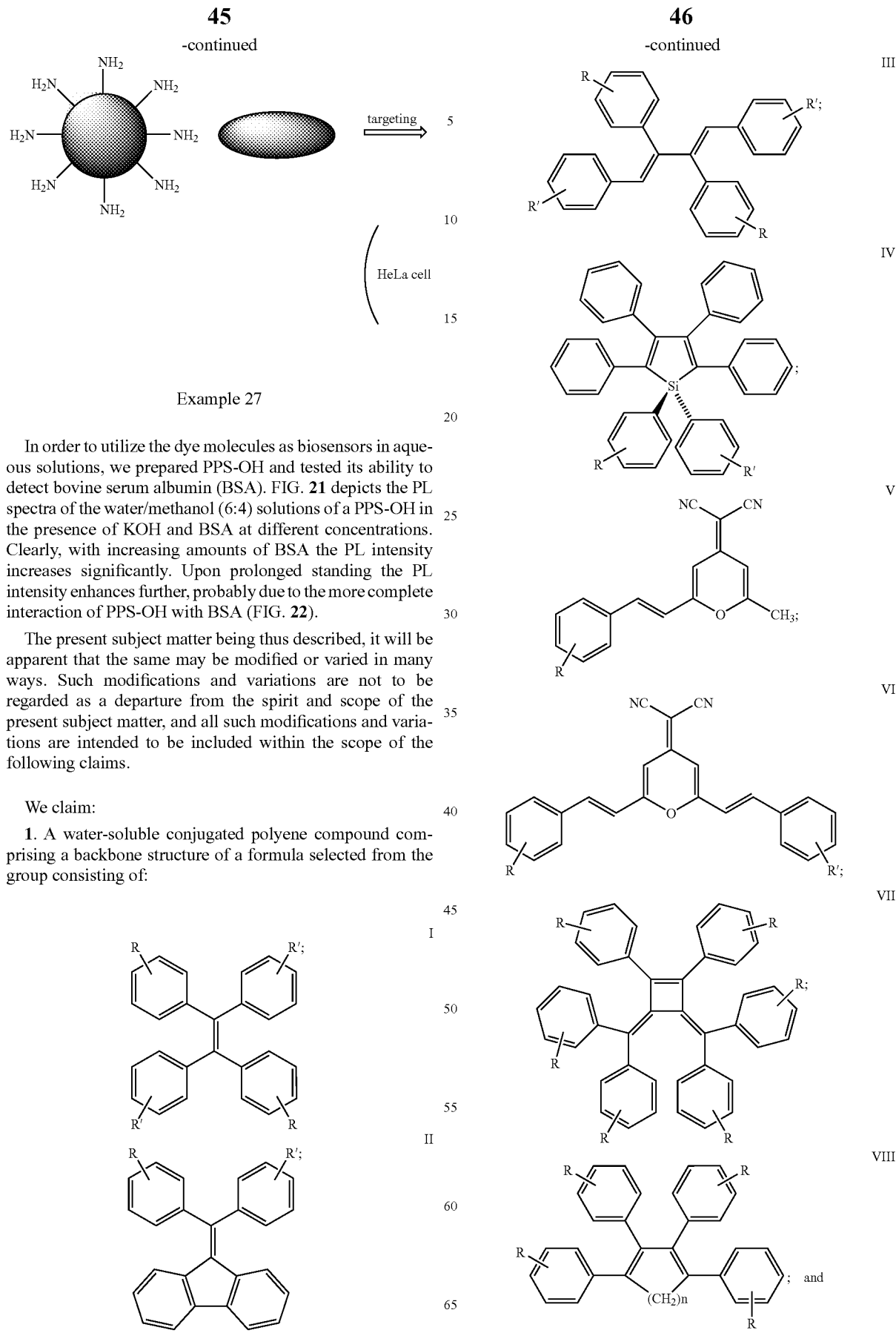

Example 27

Figure 21:
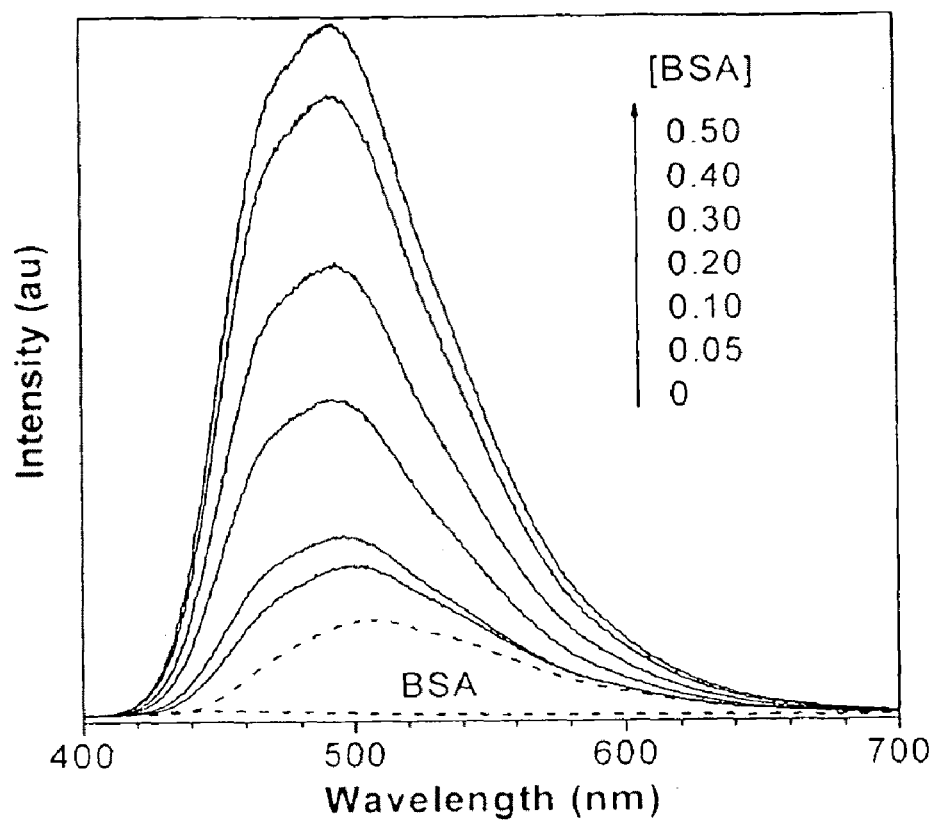
FIG. 21 is PL spectra of the water/methanol (6:4) solutions of a PPS-OH ($5.7 \times 10^{-5}$ M) in the presence of KOH ($8.4 \times 10^{-4}$ M) and BSA (at concentrations given in the figure), as described in Example 27.
Figure 22:
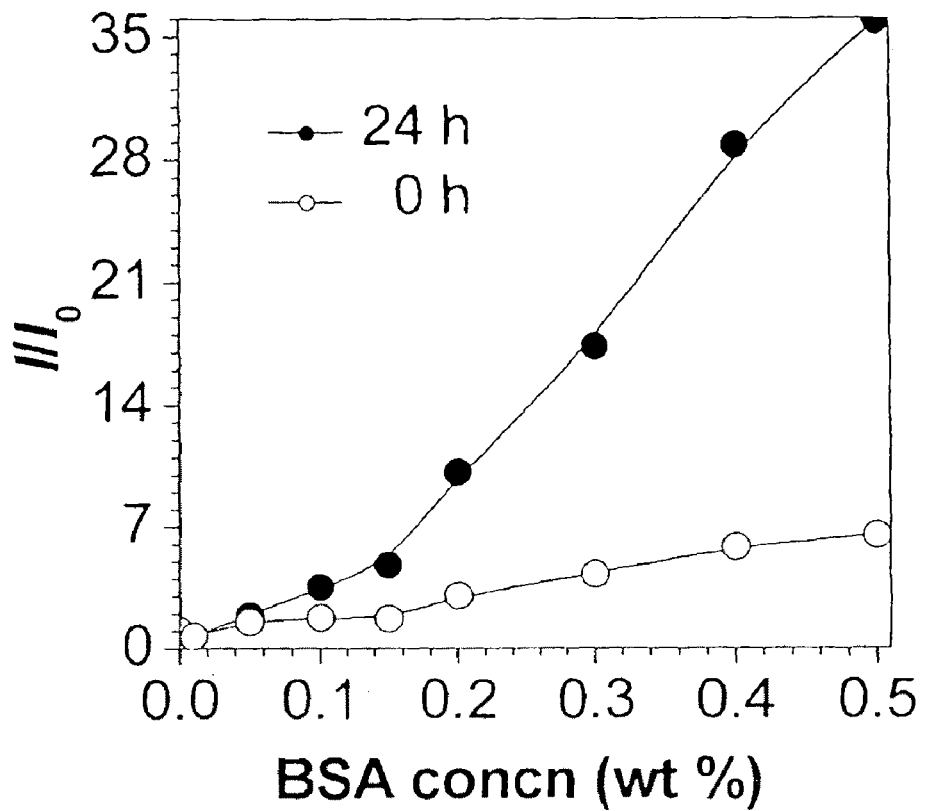
FIG. 22 shows the dependency of fluorescence intensity of PPS-OH on BSA concentration as described in Example 27.

In order to utilize the dye molecules as biosensors in aqueous solutions, we prepared PPS-OH and tested its ability to detect bovine serum albumin (BSA). FIG. 21 depicts the PL spectra of the water/methanol (6:4) solutions of a PPS-OH in the presence of KOH and BSA at different concentrations. Clearly, with increasing amounts of BSA the PL intensity increases significantly. Upon prolonged standing the PL intensity enhances further, probably due to the more complete interaction of PPS-OH with BSA (FIG. 22).

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A water-soluble conjugated polyene compound comprising a backbone structure of a formula selected from the group consisting of:

-continued

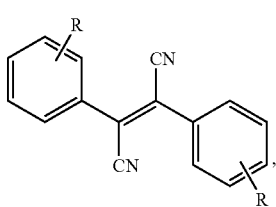

wherein,

R and R' are independently selected from X, B(OH)$_2$, (X)$_n$COOR", (X)$_n$COOH, (X)$_n$NH$_2$, (X)$_n$NHR", (X)$_n$NR"$_2$, (X)$_n$N+R"$_3$Br$^-$, (X)$_n$OH, (X)$_n$SH, (X)$_n$SO$_3^-$Na$^+$,

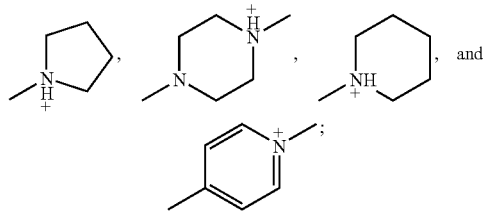

X is selected from (CH$_2$)$_n$ (n is not 0), O(CH$_2$)$_n$, NH(CH$_2$)$_n$, N[(CH$_2$)$_n$]$_2$, and (OCH$_2$CH$_2$)$_n$;

R" is selected from R, R', (CH$_2$)$_n$CH$_3$, CONH—X—, COO—X—, C$_6$H$_5$—R, —CH$_2$—C$_6$H$_5$, and C$_6$H$_5$; and wherein n=0 to 20, and the compound is water-soluble and exhibits aggregation induced emission.

2. The water-soluble conjugated polyene compound of claim 1, wherein the molecule has a backbone structure of a formula I.

3. The water-soluble conjugated polyene compound of claim 1, wherein the molecule has a backbone structure of formula II.

4. The water-soluble conjugated polyene compound of claim 1, wherein the molecule has a backbone structure of formula III.

5. The water-soluble conjugated polyene compound of claim 1, wherein the molecule has a backbone structure of formula IV.

6. The water-soluble conjugated polyene compound of claim 1, wherein the molecule has a backbone structure of formula V.

7. The water-soluble conjugated polyene compound of claim 1, wherein the molecule has a backbone structure of formula VI.

8. The water-soluble conjugated polyene compound of claim 1, wherein the compound does not exhibit aggregation induced quenching.

9. A method for detecting the presence or absence of a target biomacromolecule in a biological sample, comprising contacting the biological sample with the water-soluble conjugated polyene compound of claim 1, and detecting luminescence.

10. The method of claim 9, wherein the biological sample is selected from the group consisting of a tissue sample, a cell sample, blood, saliva, spinal fluid, lymph fluid, vaginal fluid, seminal fluid, and urine.

11. A sensor device for detecting the presence or absence of a target biomacromolecule, comprising a holder and a detecting molecule comprising the water-soluble conjugated polyene compound of claim 1, the detecting molecule being held in place by the holder and being accessible to the target molecule or substance.

12. Water-dispersible, fluorescent, polymeric particles, comprising:
the water-soluble conjugated polyene compound of claim 2; and
a polymer comprising one or more ethylenically unsaturated monomers.

13. The water-dispersible, fluorescent, polymeric particles of claim 12, wherein R is H and R' is selected from H, OH, COOH, and NH$_2$.

14. The water-dispersible, fluorescent, polymeric particles of claim 12, wherein the polymer is a homopolymer or a copolymer comprising one or more monomers selected from the group consisting of a vinylaromatic monomer, an ethylenic monomer, an alkanoic acid or ester or anhydride, and an ethylchic acid or ester, wherein one or more of the one or more monomers is optionally functionalized.

15. The water-dispersible, fluorescent, polymeric particles of claim 14, comprising at least one functionalized monomer.

16. The water-dispersible, fluorescent, polymeric particles of claim 12, wherein the one or more ethylenically unsaturated monomers comprise methyl methacrylate, butyl acrylate and 2-hydroxyethyl methacrylate.

17. The water-dispersible, fluorescent, polymeric particles of claim 16, wherein the methyl methacrylate, butyl acrylate, and 2-hydroxyethyl methacrylate are present in a ratio of from 4:5:1 to 5:4:1.

18. The water-dispersible, fluorescent, polymeric particles of claim 12, wherein the one or more ethylenically unsaturated monomers comprise methyl methacrylate, butyl acrylate, and acrylic acid and/or acrylamide.

19. The water-dispersible, fluorescent, polymeric particles of claim 15, wherein the ratio of monomer to functionalized monomer is in the range of from about 7:1 to about 11:1.

20. The water-dispersible, fluorescent, polymeric particles of claim 12, having a glass transition temperature below room temperature.

21. The water-dispersible, fluorescent, polymeric particles of claim 12, comprising microparticles.

22. The water-dispersible, fluorescent, polymeric particles of claim 21, wherein the microparticles comprise a mean diameter in the range of from about 0.01 µm to about 5 µm.

23. The water-dispersible, fluorescent, polymeric particles of claim 22, wherein greater than about 50% of the microparticles comprise a mean particle diameter in the range of from about 10 nm to about 500 nm.

24. A method for making the water-dispersible, fluorescent, polymeric particles of claim 12, comprising:
dissolving the water-soluble conjugated polyene compound in the one or more monomers to form a monomer solution;
providing an aqueous composition comprising one or more members selected from the group consisting of a surfactant, a stabilizer and a cross-linking agent;
adding the monomer solution dropwise to the aqueous composition to form a mixture; and
polymerizing the mixture to produce the water-dispersible, fluorescent, polymeric particles.

25. The water-dispersible, fluorescent, polymeric particle of claim 12, comprising a formulation selected from a bioprobe, a coating, a paint, a flexible free-standing film, a cosmetic, a fluidic tracer, or a marker.

* * * * *